United States Patent
Splett et al.

(10) Patent No.: US 11,724,113 B2
(45) Date of Patent: Aug. 15, 2023

(54) METHOD AND APPARATUS FOR ESTABLISHING PARAMETERS FOR CARDIAC EVENT DETECTION

(71) Applicant: Medtronic, Inc., Minneapolis, MN (US)

(72) Inventors: Vincent E. Splett, Apple Valley, MN (US); Keelia Doyle, Minneapolis, MN (US); Greggory R. Herr, Blaine, MN (US); Juliana E. Pronovici, New Hope, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 550 days.

(21) Appl. No.: 16/703,047

(22) Filed: Dec. 4, 2019

(65) Prior Publication Data

US 2020/0179707 A1    Jun. 11, 2020

Related U.S. Application Data

(60) Provisional application No. 62/776,034, filed on Dec. 6, 2018, provisional application No. 62/776,027, filed on Dec. 6, 2018.

(51) Int. Cl.
| | |
|---|---|
| *A61N 1/362* | (2006.01) |
| *A61N 1/375* | (2006.01) |
| *A61B 5/00* | (2006.01) |
| *A61B 5/021* | (2006.01) |
| *A61N 1/368* | (2006.01) |

(Continued)

(52) U.S. Cl.
CPC ........ *A61N 1/37512* (2017.08); *A61B 5/0006* (2013.01); *A61B 5/024* (2013.01); *A61B 5/02116* (2013.01); *A61B 5/02125* (2013.01); *A61B 5/721* (2013.01); *A61B 5/7282* (2013.01);

(Continued)

(58) Field of Classification Search
CPC ............ A61N 1/36578; A61N 1/36542; A61N 1/3682; A61N 1/3956; A61N 1/36585
See application file for complete search history.

(56) References Cited

U.S. PATENT DOCUMENTS

| | | |
|---|---|---|
| 4,485,813 A | 12/1984 | Anderson et al. |
| 5,052,388 A | 10/1991 | Sivula et al. |

(Continued)

FOREIGN PATENT DOCUMENTS

WO    2018165289 A1    9/2018

OTHER PUBLICATIONS (PCT/US2019/064657) PCT Notification of Transmittal of the International Search Report and the Written Opinion of the International Searching Authority, dated Feb. 28, 2020, 8 pages.

(Continued)

*Primary Examiner* — Michael J D'Abreu

(57) ABSTRACT

A pacemaker having a motion sensor is configured to set atrial event sensing parameters used for sensing atrial systolic events from a motion signal produced by the motion sensor. The pacemaker sets at least one atrial event sensing parameter by identifying ventricular electrical events and setting a sensing window following each of the ventricular electrical events. The pacemaker may determine a feature of the motion signal produced by the motion sensor during each of the sensing windows and set the atrial event sensing parameter based on the determined features.

39 Claims, 15 Drawing Sheets

(51) Int. Cl.
    *A61B 5/024*        (2006.01)
    *A61N 1/36*         (2006.01)
(52) U.S. Cl.
    CPC ....... *A61N 1/3682* (2013.01); *A61N 1/36175*
                (2013.01); *A61N 1/36843* (2017.08)

(56) References Cited

U.S. PATENT DOCUMENTS

| | | |
|---|---|---|
| 5,292,341 A | 3/1994 | Snell |
| 5,480,412 A | 1/1996 | Mouchawar et al. |
| 5,507,782 A | 4/1996 | Kieval et al. |
| 5,593,431 A | 1/1997 | Sheldon |
| 5,683,432 A | 11/1997 | Goedeke et al. |
| 5,885,471 A | 3/1999 | Ruben et al. |
| 6,044,297 A | 3/2000 | Sheldon et al. |
| 6,295,471 B1 | 9/2001 | Bornzin et al. |
| 6,625,490 B1 | 9/2003 | McClure et al. |
| 7,062,328 B1 | 6/2006 | Levine et al. |
| 7,130,681 B2 | 10/2006 | Gebhardt et al. |
| 7,483,745 B2 | 1/2009 | Amblard |
| 7,848,807 B2 | 12/2010 | Wang |
| 7,869,876 B2 | 1/2011 | Prakash et al. |
| 8,214,036 B2 | 7/2012 | Casset |
| 8,233,981 B2 | 7/2012 | Casset |
| 8,380,308 B2 | 2/2013 | Rosenberg et al. |
| 8,433,409 B2 | 4/2013 | Johnson et al. |
| 8,478,388 B2 | 7/2013 | Nguyen et al. |
| 8,532,785 B1 | 9/2013 | Crutchfield et al. |
| 8,541,131 B2 | 9/2013 | Lund et al. |
| 8,700,181 B2 | 4/2014 | Bornzin et al. |
| 8,909,329 B2 | 12/2014 | Prakash et al. |
| 8,923,963 B2 | 12/2014 | Bonner et al. |
| 8,996,109 B2 | 3/2015 | Karst et al. |
| 9,272,146 B2 | 3/2016 | Anselmi |
| 9,278,218 B2 | 3/2016 | Karst et al. |
| 9,775,982 B2 | 10/2017 | Grubac et al. |
| 10,080,900 B2 | 9/2018 | Ghosh et al. |
| 10,207,116 B2 | 2/2019 | Sheldon et al. |
| 10,286,214 B2 | 5/2019 | Demmer et al. |
| 10,328,270 B2 | 6/2019 | Demmer et al. |
| 10,449,366 B2 | 10/2019 | Splett et al. |
| 10,532,212 B2 | 1/2020 | Splett et al. |
| 2012/0095521 A1 | 4/2012 | Hintz |
| 2015/0173655 A1 | 6/2015 | Demmer et al. |
| 2016/0023000 A1 | 1/2016 | Cho et al. |
| 2016/0114161 A1 | 4/2016 | Amblard et al. |
| 2017/0274213 A1* | 9/2017 | Ghosh .................. A61N 1/0573 |
| 2018/0154154 A1* | 6/2018 | Sheldon ............. A61N 1/37205 |
| 2018/0161580 A1 | 6/2018 | Demmer et al. |

OTHER PUBLICATIONS (PCT/US2019/064653) PCT Notification of Transmittal of the International Search Report and the Written Opinion of the International Searching Authority, dated Jun. 24, 2020, 17 pages.
(PCT/US2019/064653) PCT Invitation to Pay Additional Fees, dated Mar. 4, 2020, 16 pages.

* cited by examiner

METHOD AND APPARATUS FOR ESTABLISHING PARAMETERS FOR CARDIAC EVENT DETECTION

REFERENCE TO RELATED APPLICATIONS

This application claims the benefit of U.S. Patent Application No. 62/776,027, filed provisionally on Dec. 6, 2018, and U.S. Patent Application No. 62/776,034, filed provisionally on Dec. 6, 2018, both of which are incorporated herein by reference in their entirety.

TECHNICAL FIELD

This disclosure relates to a medical device and method for establishing parameters for detecting cardiac events from a motion sensor signal.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, some patients may benefit from atrial and ventricular (dual chamber) sensing for providing atrial-synchronized ventricular pacing in order to maintain a regular heart rhythm.

SUMMARY

The techniques of this disclosure generally relate to a pacemaker having a motion sensor producing a motion signal including ventricular and atrial event signals. The pacemaker is configured to sense atrial events from the motion signal. The sensed atrial events may be used for controlling atrial synchronized ventricular pacing pulses delivered by the pacemaker in some examples. A pacemaker operating according to the techniques disclosed herein determines one or more atrial event sensing parameters used for sensing the atrial event signals by determining a feature of the motion signal and setting the atrial event sensing parameter based on the feature determined over multiple ventricular cycles. In some examples, the atrial event sensing parameter is set based on a distribution of the feature, e.g., based on a percentile or a median or other measure of centeredness of the distribution.

In one example, the disclosure provides a pacemaker including a pulse generator configured to generate pacing pulses for delivery to a ventricle of a patient's heart via electrodes coupled to the pacemaker, a sensing circuit comprising an R-wave detector for sensing R-waves from a cardiac electrical signal received via electrodes coupled to the pacemaker, a motion sensor configured to produce a motion signal comprising an atrial event signal corresponding to an atrial systolic event, and a control circuit coupled to the motion sensor, the sensing circuit and the pulse generator. The control circuit is configured to identify ventricular electrical events, which may be sensed R-waves and/or generated ventricular pacing pulses. Following each of the ventricular electrical events, the control circuit may set a sensing window, determine a feature of the motion signal during each of the sensing windows and set an atrial event sensing parameter based on the determined features. The pacemaker may sense the atrial systolic event from the motion signal based on the atrial event sensing parameter and produce an atrial sensed event signal in response to sensing the atrial systolic event. In some examples, the control circuit may start an atrioventricular pacing interval in response to sensing the atrial systolic event and control the pulse generator to generate a ventricular pacing pulse in response to the atrioventricular pacing interval expiring.

In another example, the disclosure provides a method performed by a pacemaker. The method includes producing a motion signal comprising an atrial event signal corresponding to an atrial systolic event, identifying ventricular electrical events and setting a sensing window following each of the ventricular electrical events. The method further includes determining a feature of a motion signal produced by a motion sensor of the pacemaker during each of the sensing windows and setting an atrial event sensing parameter based on the determined features. The method may further include sensing an atrial systolic event from the motion signal based on the atrial event sensing parameter and producing an atrial sensed event signal in response to sensing the atrial systolic event. In some examples, the method includes starting an atrioventricular pacing interval in response to sensing the atrial event and delivering a ventricular pacing pulse in response to the atrioventricular pacing interval expiring.

In another example, the disclosure provides a non-transitory, computer-readable storage medium comprising a set of instructions which, when executed by a control circuit of a pacemaker, cause the pacemaker to produce a motion signal comprising an atrial event signal corresponding to an atrial systolic event, identify ventricular electrical events, set a sensing window following each of the ventricular electrical events, determine a feature of a motion signal produced by a motion sensor of the pacemaker during each of the sensing windows, and set an atrial event sensing parameter based on the determined features. The instructions further cause the pacemaker to sense the atrial systolic event from the motion signal based on the atrial event sensing parameter and produce an atrial sensed event signal in response to sensing the atrial systolic event. In some examples, the instructions further cause the pacemaker to start an atrioventricular pacing interval in response to the atrial sensed event signal and generate a ventricular pacing pulse in response to the atrioventricular pacing interval expiring.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

In general, this disclosure describes techniques for establishing cardiac event sensing parameters by an implantable medical device. As described below, atrial systolic events may be sensed from a signal produced by a motion sensor that includes an atrial systolic event signal corresponding to atrial mechanical contraction and the active filling phase of the ventricle, sometimes referred to as the "atrial kick." The atrial event sensing parameters may include selecting a vector signal of the motion sensor, a sensing threshold amplitude, and time windows during which an atrial event can be sensed. The techniques disclosed herein provide techniques for sensing atrial events by a ventricular pacemaker, which may be wholly implantable within a ventricular heart chamber and having a motion sensor for producing an intraventricular motion signal. In this way, atrial events can be detected from within the ventricle for use in controlling atrial synchronized ventricular pacing, for example. Atrial-synchronized ventricular pacing pulses can be delivered by a pacemaker implanted in the ventricle without requiring a sensor in or on the atria of the patient's heart for detecting atrial events.

Figure 1:
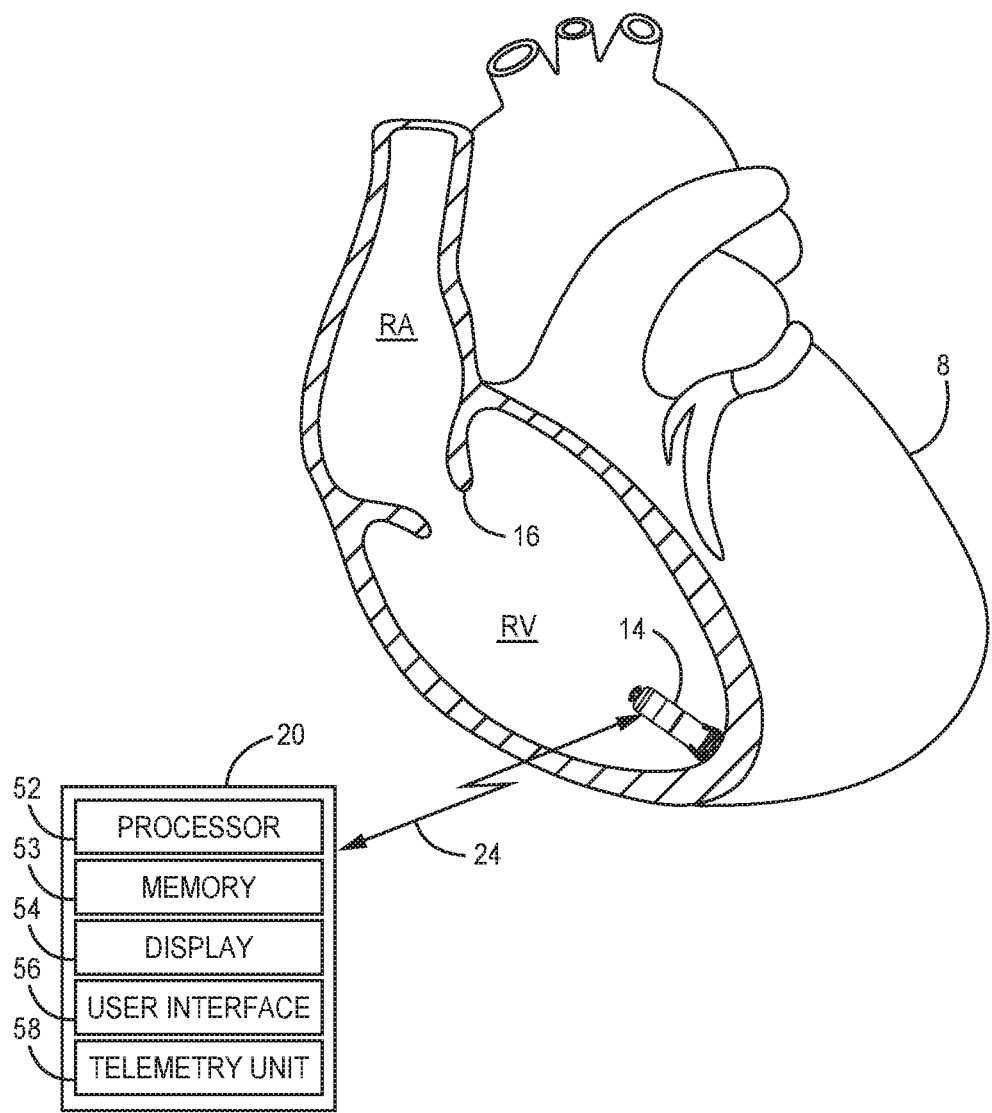
FIG. 1 is a conceptual diagram illustrating a medical device system that may be used to sense cardiac electrical signals and motion signals induced by cardiac motion and flowing blood and provide pacing therapy to a patient's heart.

FIG. 1 is a conceptual diagram illustrating an implantable medical device (IMD) system 10 that may be used to sense cardiac electrical signals and motion signals induced by cardiac motion and flowing blood and provide pacing therapy to a patient's heart 8. IMB system 10 includes a ventricular intracardiac pacemaker 14. Pacemaker 14 may be a transcatheter intracardiac pacemaker which is adapted for implantation wholly within a heart chamber, e.g., wholly within the right ventricle (RV) or wholly within the left ventricle (LV) of heart 8 for sensing cardiac signals and delivering ventricular pacing pulses. Pacemaker 14 may be reduced in size compared to subcutaneously implanted pacemakers and may be generally cylindrical in shape to enable transvenous implantation via a delivery catheter.

Pacemaker 14 is shown positioned in the RV, along an endocardial wall, e.g., near the RV apex though other locations are possible. The techniques disclosed herein are not limited to the pacemaker location shown in the example of FIG. 1 and other positions within heart 8 are possible. For example, ventricular intracardiac pacemaker 14 may be positioned in the LV and configured to detect cardiac motion signals and deliver atrial-synchronized ventricular pacing to the LV using the techniques disclosed herein. Pacemaker 14 may be positioned within the RV or LV to provide respective right ventricular or left ventricular pacing and for sensing cardiac motion signals by a motion sensor within the ventricular chamber.

Pacemaker 14 is capable of producing electrical stimulation pulses, e.g., pacing pulses, delivered to heart 8 via one or more electrodes on the outer housing of the pacemaker. Pacemaker 14 is configured to deliver RV pacing pulses and sense an RV cardiac electrical signal using housing based electrodes for producing an RV electrogram (EGM) signal. The cardiac electrical signals may be sensed using the housing based electrodes that are also used to deliver pacing pulses to the RV.

Pacemaker 14 is configured to control the delivery of ventricular pacing pulses to the RV in a manner that promotes synchrony between atrial activation and ventricular activation, e.g., by maintaining a target atrioventricular (AV) interval between atrial events and ventricular pacing pulses. That is, pacemaker 14 controls pacing pulse delivery to maintain a desired AV interval between atrial contractions corresponding to atrial systole and ventricular pacing pulses delivered to cause ventricular depolarization and ventricular systole.

According to the techniques described herein, atrial systolic events producing the active ventricular filling phase are detected by pacemaker 14 from a motion sensor such as an accelerometer enclosed by the housing of pacemaker 14. The motion signal produced by an accelerometer implanted within a ventricular chamber, which may be referred to as an "intraventricular motion signal," includes motion signals caused by ventricular and atrial events. For example, acceleration of blood flowing into the RV through the tricuspid valve 16 between the RA and RV caused by atrial systole, and referred to as the "atrial kick," may be detected by pacemaker 14 from the signal produced by an accelerometer included in pacemaker 14. Other motion signals that may be detected by pacemaker 14, such as motion caused by ventricular contraction and passive ventricular filling are described below in conjunction with FIG. 4.

Atrial P-waves that are attendant to atrial depolarization are relatively low amplitude signals in the near-field ventricular cardiac electrical signal received by pacemaker 14 (e.g., compared to the near-field R-wave) and therefore can be difficult to reliably detect from the cardiac electrical signal acquired by pacemaker 14 implanted in a ventricular chamber. Atrial-synchronized ventricular pacing by pacemaker 14 or other functions that rely on atrial sensing may not be reliable when based solely on a cardiac electrical signal received by pacemaker 14. According to the techniques disclosed herein, pacemaker 14 includes a motion sensor, such as an accelerometer, and is configured to detect an atrial event corresponding to atrial mechanical activation or atrial systole from a signal produced by the motion sensor. Ventricular pacing pulses may be synchronized to the atrial event that is detected from the motion sensor signal by setting a programmable AV pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event.

A target AV interval may be a default value or a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by pacemaker 14 and the motion sensor signal received by pacemaker 14.

Pacemaker 14 may be capable of bidirectional wireless communication with an external device 20 for programming the AV pacing interval and other pacing control parameters as well as cardiac event sensing parameters, which may be utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemaker 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemaker 14 using external device 20.

External device 20 may include a processor 52, memory 53, display 54, user interface 56 and telemetry unit 58. Processor 52 controls external device operations and processes data and signals received from pacemaker 14. Display unit 54 may generate a display, which may include a graphical user interface, of data and information relating to pacemaker functions to a user for reviewing pacemaker operation and programmed parameters as well as cardiac electrical signals, cardiac motion signals or other physiological data that may be acquired by pacemaker 14 and transmitted to external device 20 during an interrogation session.

User interface 56 may include a mouse, touch screen, key pad or the like to enable a user to interact with external device 20 to initiate a telemetry session with pacemaker 14 for retrieving data from and/or transmitting data to pacemaker 14, including programmable parameters for controlling cardiac event sensing and therapy delivery. Telemetry unit 58 includes a transceiver and antenna configured for bidirectional communication with a telemetry circuit included in pacemaker 14 and is configured to operate in conjunction with processor 52 for sending and receiving data relating to pacemaker functions via communication link 24.

At the time of implant, during patient follow-up visits, or any time after pacemaker implantation, pacemaker 14 may perform a set-up procedure to establish parameters used in detecting atrial events from the motion sensor signal. The patient may be standing, sitting, lying down or ambulatory during the process. The set-up procedure may include acquiring motion sensor signal data and generating distributions of motion sensor signal features for establishing atrial event sensing parameters. Motion sensor signal data may be transmitted to external device 20 and displayed on display unit 54 of external device 20 in the form of a histogram in some examples. The atrial event sensing parameters established based on the motion sensor signal data may be set automatically or may be transmitted to external device 20 for generating a display on display unit 54 as recommended parameters, allowing a clinician to review and accept or modify the recommended parameters, e.g., using user interface 56.

In some examples, external device processor 52 may execute operations disclosed herein for establishing a starting value of an atrial event sensing parameter based on data retrieved from pacemaker 14. Processor 52 may cause display unit 54 to generate a display of data relating to a motion sensor signal, including histogram distributions of metrics determined from a cardiac motion signal for use in selecting starting values of atrial event sensing control parameters. Display unit 54 may be a graphical user interface that enables a user to interact with the display, e.g., for selecting various displays or information for viewing. In some examples, a user may select one or more atrial event sensing control parameter settings to be automatically established by pacemaker 14 and/or may program starting sensing control parameters or other programmable parameters for controlling sensor operation and therapy delivery. Processing circuitry included in pacemaker 14 and/or processor 52 may determine starting values for one or more atrial systolic event sensing control parameters based on data acquired from motion sensor signals produced by an accelerometer included in pacemaker 14 and various thresholds and criteria, which may include user programmable thresholds or criteria used in setting the starting parameter values.

External device telemetry unit 58 is configured for bidirectional communication with implantable telemetry circuitry included in pacemaker 14. Telemetry unit 58 establishes a wireless communication link 24 with pacemaker 14. Communication link 24 may be established using a radio frequency (RF) link such as BLUETOOTH®, Wi-Fi, Medical Implant Communication Service (MICS) or other communication bandwidth. In some examples, external device 20 may include a programming head that is placed proximate pacemaker 14 to establish and maintain a communication link 24, and in other examples external device 20 and pacemaker 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

It is contemplated that external device 20 may be in wired or wireless connection to a communications network via a telemetry circuit that includes a transceiver and antenna or via a hardwired communication line for transferring data to a centralized database or computer to allow remote management of the patient. Remote patient management systems including a centralized patient database may be configured to utilize the presently disclosed techniques to enable a clinician to review EGM, motion sensor signal, and marker channel data and authorize programming of sensing and therapy control parameters in pacemaker 14, e.g., after viewing a visual representation of EGM, motion sensor signal and marker channel data.

Figure 2:
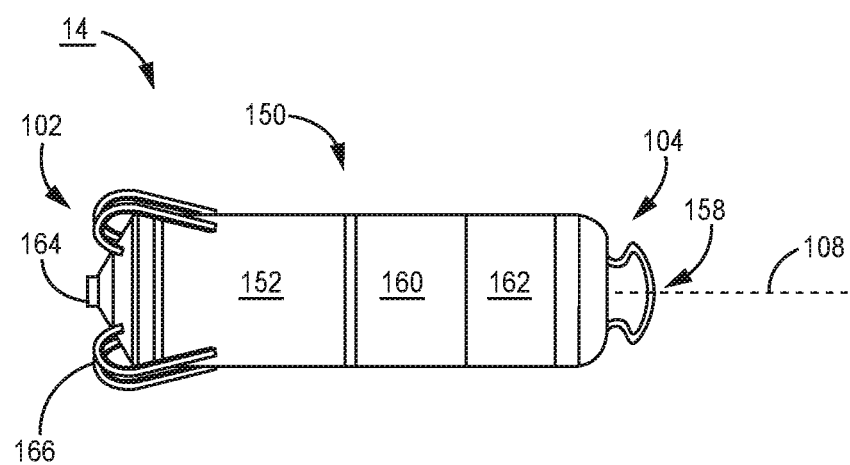
FIG. 2 is a conceptual diagram of the intracardiac pacemaker shown in FIG. 1.

FIG. 2 is a conceptual diagram of the intracardiac pacemaker 14 shown in FIG. 1. Pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 defining a ring electrode that is electrically isolated from the other portions of the housing 150 as generally shown in FIG. 2. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting atrial systolic events, e.g., for use in controlling the timing ventricular pacing pulses, as described below.

The accelerometer may be a three-dimensional accelerometer. In some examples, the accelerometer may have one "longitudinal" axis that is parallel to or aligned with the longitudinal axis 108 of pacemaker 14 and two orthogonal axes that extend in radial directions relative to the longitudinal axis 108. Practice of the techniques disclosed herein, however, are not limited to a particular orientation of the accelerometer within or along housing 150. In other examples, a one-dimensional accelerometer may be used to obtain an intracardiac motion signal from which atrial systolic events are detected. In still other examples, a two dimensional accelerometer or other multi-dimensional accelerometer may be used. Each axis of a single or multi-dimensional accelerometer may be defined by a piezoelectric element, micro-electrical mechanical system (MEMS) device or other sensor element capable of producing an electrical signal in response to changes in acceleration imparted on the sensor element, e.g., by converting the acceleration to a force or displacement that is converted to the electrical signal. In a multi-dimensional accelerometer, the sensor elements may be arranged orthogonally with each sensor element axis orthogonal relative to the other sensor element axes. Orthogonal arrangement of the elements of a multi-axis accelerometer, however, is not necessarily required.

Each sensor element may produce an acceleration signal corresponding to a vector aligned with the axis of the sensor element. As described below, techniques disclosed herein include selecting a vector signal of a multi-dimensional accelerometer (also referred to as a "multi-axis" accelerometer) for use in sensing atrial systolic events. In some cases one, two or all three axis signals produced by a three dimensional accelerometer may be selected as a vector signal for use in detecting atrial systolic events, e.g., for controlling atrial-synchronized ventricular pacing delivered by pacemaker 14.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned U.S. Pat. No. 9,775,872 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 3:
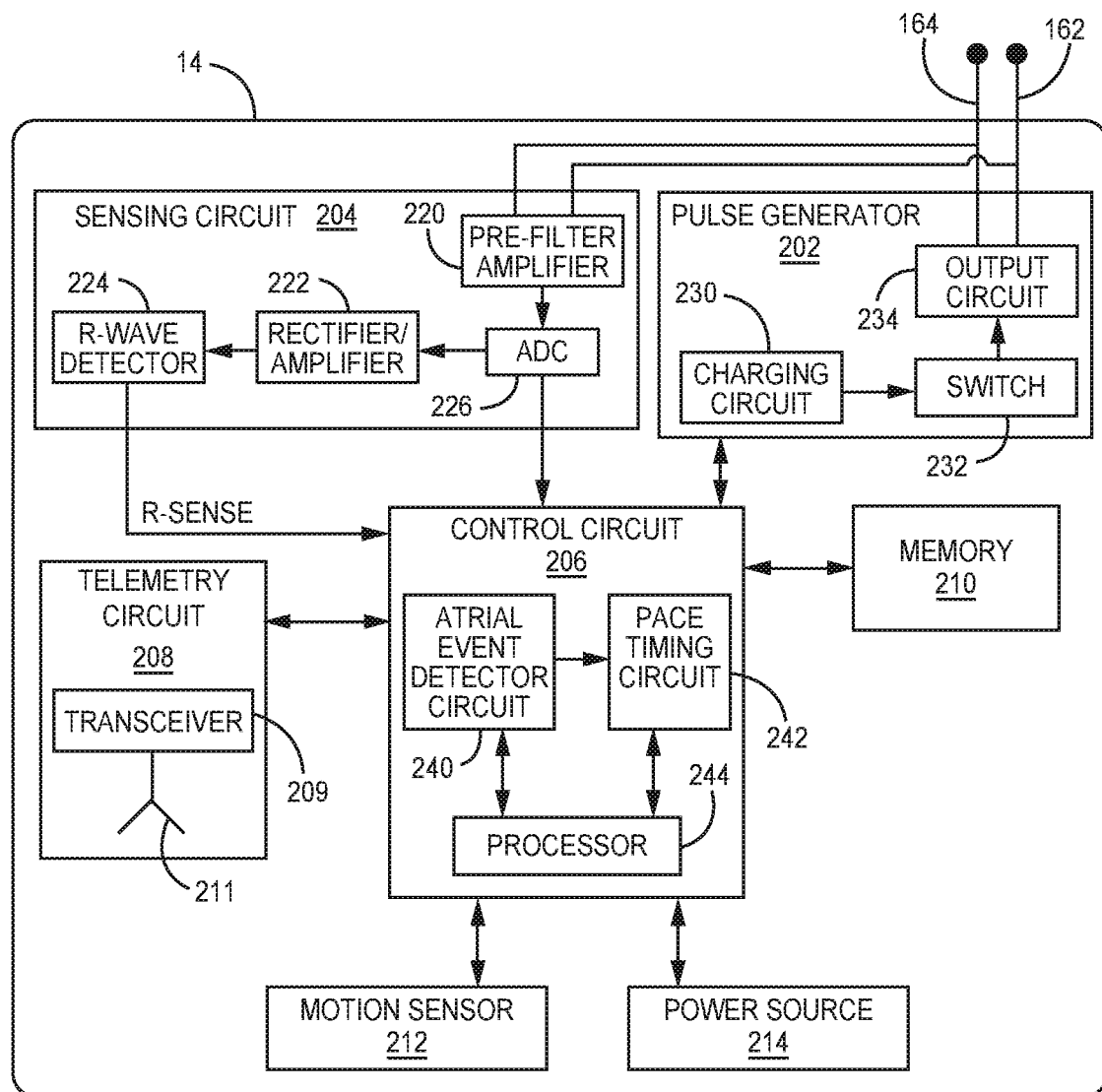
FIG. 3 is a schematic diagram of an example configuration of the pacemaker shown in FIG. 1.

FIG. 3 is a schematic diagram of an example configuration of pacemaker 14 shown in FIG. 1. Pacemaker 14 includes a pulse generator 202, a cardiac electrical signal sensing circuit 204, a control circuit 206, memory 210, telemetry circuit 208, motion sensor 212 and a power source 214. The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Motion sensor 212 may include an accelerometer in the examples described herein. Motion sensor 212 is not limited to being an accelerometer, however, and other motion sensors may be utilized successfully in pacemaker 14 for detecting cardiac motion signals according to the techniques described herein. Examples of motion sensors that may be implemented in motion sensor 212 include piezoelectric sensors and MEMS devices.

Motion sensor 212 may include a multi-axis sensor, e.g., a two-dimensional or three-dimensional sensor, with each axis providing an axis signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. The motion sensor 212 may include one or more filter, amplifier, rectifier, analog-to-digital converter (ADC) and/or other components for producing a motion signal that is passed to control circuit 206. For example, each vector signal produced by each individual axis of a multi-axis accelerometer may be filtered by a high pass filter, e.g., a 10 Hz high pass filter. The filtered signal may be digitized by an ADC and rectified for use by atrial event detector circuit 240 for detecting atrial systolic events. The high pass filter may be lowered (e.g., to 5 Hz) if needed to detect atrial signals that have lower frequency content. In some examples, high pass filtering is performed with no low pass filtering. In other examples, each accelerometer axis signal is filtered by a low pass filter, e.g., a 30 Hz low pass filter, with or without high pass filtering.

One example of an accelerometer for use in implantable medical devices that may be implemented in conjunction with the techniques disclosed herein is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for establishing atrial sensing control parameters and for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave sensing threshold, which may be an auto-adjusting threshold. When the incoming signal crosses the R-wave sensing threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. Processor 244 may provide sensing control signals to sensing circuit 204, e.g., R-wave sensing threshold, sensitivity, and various blanking and refractory intervals applied to the cardiac electrical signal for controlling R-wave sensing. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. R-wave sensed event signals may also be passed to atrial event detector circuit 240 for use in setting time windows used by control circuit 206 in detecting atrial systolic events from the motion sensor signal.

Atrial event detector circuit 240 is configured to detect atrial systolic events from a signal received from motion sensor 212. Techniques for setting time windows used in detecting atrial systolic events are described below, e.g., in conjunction with FIGS. 9-10. In some examples, one or more ventricular mechanical events may be detected from the motion sensor signal in a given cardiac cycle to facilitate positive detection of the atrial systolic event from the motion sensor signal during the ventricular cycle.

Atrial event detector circuit 240 receives a motion signal from motion sensor 212 and may start an atrial "blanking" period in response to a ventricular electrical event, e.g., an R-wave sensed event signal from sensing circuit 204 or delivery of a pacing pulse by pulse generator 202. The blanking period may correspond to a time period after the ventricular electrical event during which ventricular mechanical events, e.g., corresponding to ventricular contraction and isovolumic relaxation are expected to occur. When ventricular pacing is properly synchronized to atrial events, an atrial event is not expected to occur during the atrial blanking period, corresponding to ventricular systole. The motion signal peaks that occur during the atrial blanking period, therefore, are not sensed as atrial events. The atrial "blanking" period may be used to define a time period following a ventricular electrical event during which an atrial systolic event is not sensed by atrial event detector circuit 240. The motion sensor signal, however, is not necessarily blanked during this time period in that control circuit 206 may still receive the motion sensor signal during the atrial blanking period and may process the motion signal for sensing ventricular events during the atrial blanking period in some examples.

Atrial event detector circuit 240 determines if the motion sensor signal satisfies atrial systolic event detection criteria outside of the atrial blanking period. The motion sensor signal during the blanking period may be monitored by atrial event detector circuit 240 for the purposes of detecting ventricular mechanical events, which may be used for confirming or validating atrial systolic event detection in some examples. As such, ventricular mechanical event detection windows may be set during the atrial blanking period and may be set according to predetermined time intervals following identification of a ventricular electrical event. Atrial event detector circuit 240 may be configured to detect one or more ventricular mechanical events during respective ventricular event detection windows during the atrial blanking period. The timing and detection of the ventricular mechanical events may be used to update the atrial blanking period and/or may be used to confirm detection of the atrial event occurring subsequent to expected ventricular mechanical events.

Atrial event detector circuit 240 may set time windows corresponding to the passive ventricular filling phase and the active ventricular filling phase based on the timing of a preceding ventricular electrical event, either an R-wave sensed event signal or a ventricular pacing pulse. A motion sensor signal crossing of an atrial event sensing threshold during either of these windows may be detected as the atrial systolic event. As described below, two different atrial event sensing threshold values may be established for applying during the passive filling phase window and after the passive filling phase window (during an active filling phase window also referred to below as an "A4 window").

Atrial event detector circuit 240 passes an atrial event detection signal to processor 244 and/or pace timing circuit 242 in response to detecting an atrial event. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. One application of atrial sensed event signals produced by atrial event detector circuit 240 is for setting AV pacing intervals for controlling the timing of ventricular pacing pulses. Control circuit 206, however, may use atrial sensed event signals for other purposes.

Pace timing circuit 242 may additionally include a lower pacing rate interval timer for controlling a minimum ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate. At times, control circuit 206 may control pulse generator 202 in a non-atrial tracking ventricular pacing mode (also referred to as "asynchronous ventricular pacing") during a process for establishing sensing parameters used for detecting atrial systolic events from the motion signal. The non-atrial tracking ventricular pacing mode may be denoted as a VDI pacing mode in which ventricular pacing pulses are delivered in the absence of a sensed R-wave and inhibited in response to an R-wave sensed event signal from sensing circuit 204. Dual chamber sensing may be performed during the non-atrial tracking ventricular pacing mode by sensing ventricular electrical events by sensing circuit 204 and sensing atrial systolic events from the motion signal received by atrial event detector circuit 240 from motion sensor 212. As described below in conjunction with FIGS. 7-14, atrial event sensing parameters established during a VDI pacing mode may include an atrial event sensing vector of the motion sensor producing a signal from which the atrial systolic event is detected, the end of a passive ventricular filling window, and the atrial event sensing threshold amplitude values applied during and after the passive ventricular filling window.

Pulse generator 202 generates electrical pacing pulses that are delivered to the RV of the patient's heart via cathode electrode 164 and return anode electrode 162. In addition to providing control signals to pace timing circuit 242 and pulse generator 202 for controlling the timing of ventricular pacing pulses, processor 244 may retrieve programmable pacing control parameters, such as pacing pulse amplitude and pacing pulse width, which are passed to pulse generator 202 for controlling pacing pulse delivery. Pulse generator 202 may include charging circuit 230, switching circuit 232 and an output circuit 234.

Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or VV lower rate pacing interval) and kept closed for a programmed pacing pulse width to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial event by atrial event detector circuit 240 from the motion sensor signal and setting a pacing escape interval timer included in pace timing circuit 242, according to the techniques disclosed herein.

Power source 214 provides power to each of the other circuits and components of pacemaker 14 as required. Power source 214 may include one or more energy storage devices, such as one or more rechargeable or non-rechargeable batteries. The connections between power source 214 and other pacemaker circuits and components are not shown in FIG. 3 for the sake of clarity but are to be understood from the general block diagram of FIG. 3. For example, power source 214 may provide power as needed to charging and switching circuitry included in pulse generator 202, amplifiers, ADC 226 and other components of sensing circuit 204, telemetry circuit 208, memory 210, and motion sensor 212.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212. Providing software, hardware, and/or firmware to accomplish the described functionality in the context of any modern pacemaker, given the disclosure herein, is within the abilities of one of skill in the art.

Figure 4:
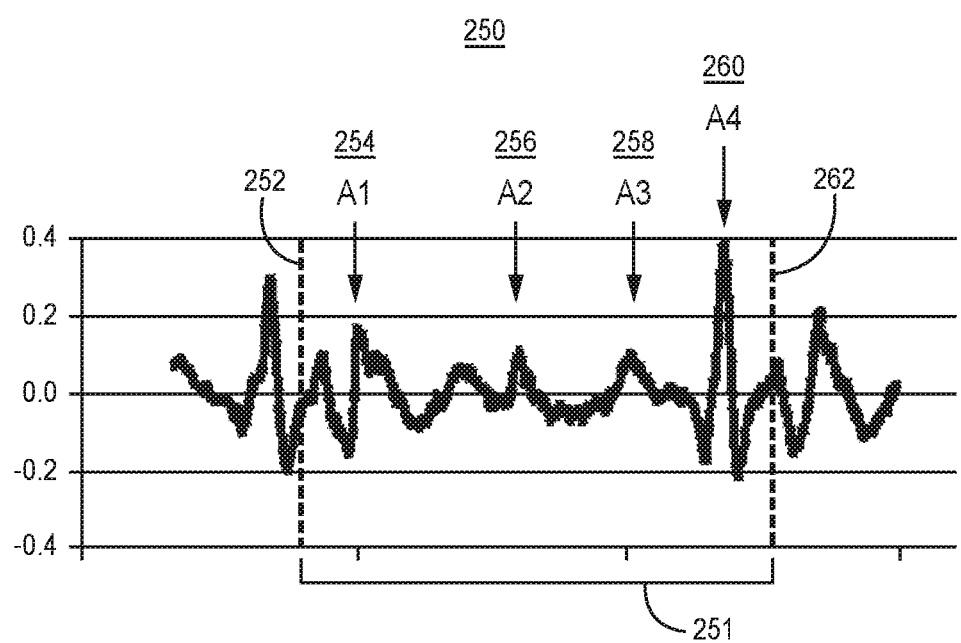
FIG. 4 is an example of a motion sensor signal that may be acquired by a motion sensor included in the pacemaker of FIG. 1 over a cardiac cycle.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pacing pulse), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 212 is implemented as an accelerometer) that occurs during ventricular contraction and marks the approximate onset of ventricular mechanical systole. The A1 event is also referred to herein as a "ventricular contraction event." The A2 event 256 is an acceleration signal that may occur with closure of the aortic and pulmonic valves, marking the approximate offset or end of ventricular mechanical systole. The A2 event may also mark the beginning of the isovolumic relaxation phase of the ventricles that occurs with aortic and pulmonic valve closure.

The A3 event 258 is an acceleration signal that occurs during passive ventricular filling and marks ventricular mechanical diastole. The A3 event is also referred to herein as the "A3 signal" and as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "A4 signal" and is the "atrial systolic event" or merely the "atrial event" that is detected from motion sensor signal 250. Atrial event detector circuit 240 detects A4 event 260. Processor 244 may control pace timing circuit 242 to trigger a ventricular pacing pulse by starting an AV pacing interval in response to detecting the A4 event 260. Control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Techniques described in conjunction with FIGS. 6-13 may be performed by pacemaker 14 for establishing parameters used for detecting A4 events, without necessarily requiring identification and discrimination of the A1-A4 events. Instead, the motion signal acquired during a non-atrial tracking ventricular pacing mode may be characterized by determining features of the motion signal during a sensing window and/or outside an atrial blanking period. Distributions of the features are used in establishing atrial event sensing parameters.

Figure 5:
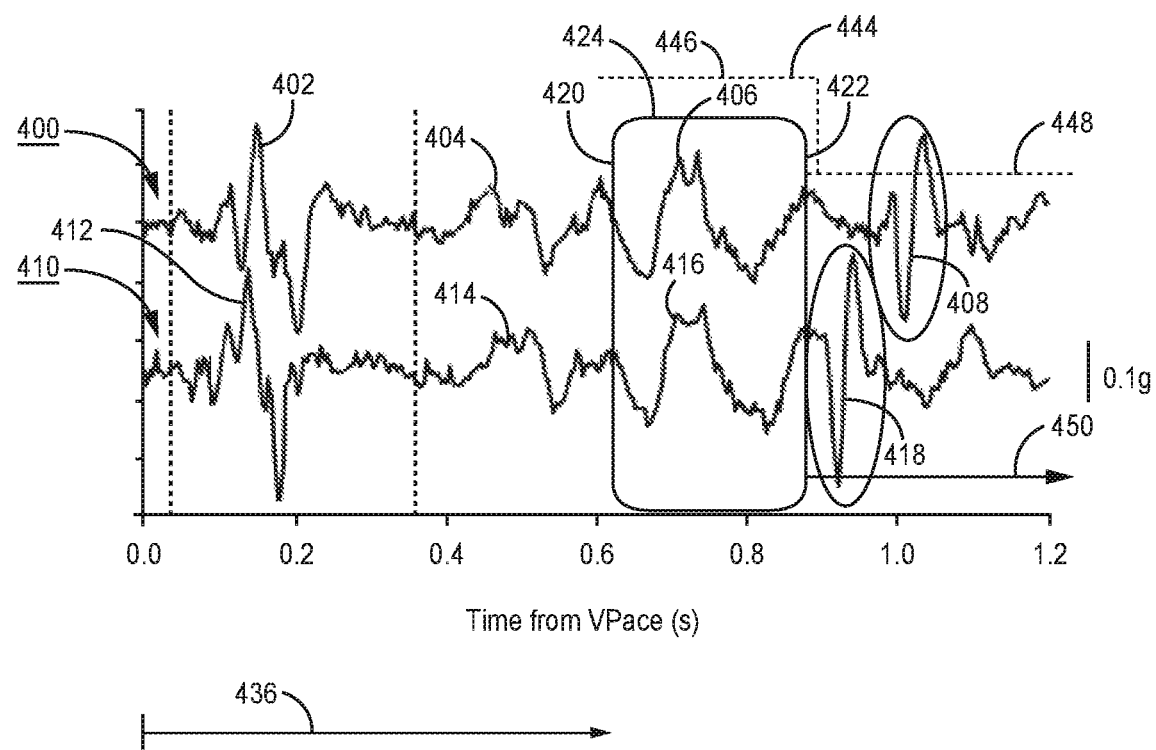
FIG. 5 is an example of motion sensor signals acquired over two different cardiac cycles.

FIG. 5 is an example of motion sensor signals 400 and 410 acquired over two different cardiac cycles. A ventricular pacing pulse is delivered at time 0.0 seconds for both cardiac cycles. The top sensor signal 400 is received over one cardiac cycle, and the bottom sensor signal 410 is received over a different cardiac cycle. The two signals 400 and 410 are aligned in time at 0.0 seconds, the time of the ventricular pacing pulse delivery. While motion signals 400 and 410 and motion signal 250 of FIG. 4 are shown as raw accelerometer signals, it is recognized that control circuit 206 may receive a digitized filtered, amplified and rectified signal from motion sensor 212 for processing and analysis as described in conjunction with the flow charts and histogram distributions presented in the accompanying drawings.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (which may mark the end of ventricular systole and the isovolumic ventricular relaxation phase) and the A3 events 406 and 416 (occurring during passive ventricular filling) are well-aligned in time. Since the A1, A2 and A3 events are ventricular events, occurring during ventricular contraction, at the end of ventricular systole and start of isovolumic ventricular relaxation and during passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of ventricular A1, A2 and A3 events to each other and the immediately preceding ventricular electrical event is expected to be consistent from beat-to-beat.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining an atrial blanking period 436 and increasing confidence in reliably detecting A4 events 408 and 418. The atrial systolic event is not detected during the atrial blanking period 436 which extends from the ventricular electrical event (at time 0.0) through an estimated onset of ventricular diastole so that the atrial blanking period 436 includes both the A1 and A2 events. An A3 window 424 may be set having a starting time 420 corresponding to the end of the post-ventricular atrial blanking period 436 and an ending time 422. The ending time 422 may be established using techniques described below in conjunction with FIGS. 9 and 10. The ending time 422 may also be considered a starting time of an A4 sensing window 450, though A4 signals may be sensed during the A3 window in some instances.

A4 events 408 and 418 may be detected based on a multi-level A4 sensing threshold 444. As seen by the lower motion sensor signal 410, the A4 event 418 may occur earlier after the A3 window 424 due to changes in atrial rate. In some instances, as the atrial rate increases, the A4 event 418 may occur within the A3 window 424. When this occurs, the A3 event 416 and the A4 event 418 may fuse as passive and active ventricular filling occur together. The fused A3/A4 event may have a high amplitude, even greater than the amplitude of either the A3 event 416 or the A4 event 418 when they occur separately. As such, in some examples a first, higher A4 sensing threshold amplitude 446 may be established for detecting an early A4 signal that is fused with the A3 signal during the A3 window 424. A second, lower A4 sensing threshold amplitude 448 may be established for detecting relatively later A4 signals, after the ending time 422 of the A3 window 424, during an A4 window 450. The A4 window 450 extends from the ending time of the A3 window 424 until the next ventricular electrical event, sensed or paced. The earliest crossing of the A4 sensing threshold 444 by the motion sensor signal after the starting time 420 of the A3 window (or after the expiration of the atrial blanking period 436) may be detected as the atrial systolic event. Techniques for establishing an early A4 sensing threshold amplitude 446 used during the A3 window 424 and a late A4 sensing threshold amplitude 448 used after the ending time 422 of the A3 window 424, during the A4 window 450, are described below in conjunction with FIGS. 11-13.

Figure 6:
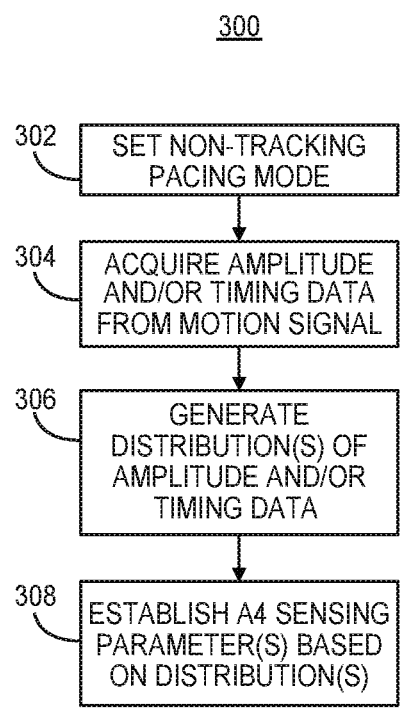
FIG. 6 is a flow chart of a method for establishing atrial event sensing parameters.

FIG. 6 is a flow chart 300 of a method for establishing atrial event sensing parameters. Control circuit 206 may perform the method of flow chart 300 to automatically select and set starting values of atrial event sensing parameters used to in sensing A4 events from the motion sensor signal during an atrial tracking ventricular pacing mode. The process of flow chart 300 may be performed by control circuit 206 upon implantation of pacemaker 14 and may be performed at other post-implant times for updating or resetting an A4 sensing parameter.

At block 302, control circuit 206 sets the pacing mode to a non-atrial tracking ventricular pacing mode (e.g., VDI) so that ventricular pacing pulses are being delivered asynchronously to atrial events. The pacing rate may be set to a nominal rate, e.g., 50 pulses per minute. In some examples, the ventricular pacing mode may be a rate responsive mode (e.g., VDIR), but the method for establishing the atrial event sensing parameters may be performed when the pacing rate is at or near the programmed lower rate, e.g., 40 to 60 pulses per minute. In a patient having AV block, atrial systolic events occur asynchronously with ventricular electrical events during the non-atrial tracking pacing mode. Ventricular electrical events will generally be delivered ventricular pacing pulses in a patient with AV block, but may include intrinsic R-waves in some instances and in a patient with AV conduction intact. As such, atrial events may course through the ventricular cardiac cycle at varying times during the VDI pacing mode.

For each available sensing vector of the multi-axis motion sensor, motion sensor signal data is acquired during the non-atrial tracking ventricular pacing mode. Aspects of the motion sensor signal outside a post-ventricular atrial blanking period (or later than a minimum A3 window starting time) may be determined to characterize motion sensor signal features over the passive and active filling phases of each ventricular cycle for each available sensing vector. For example, at block 304, control circuit 206 may determine at least one maximum motion sensor signal amplitude in each ventricular cycle (outside the post-ventricular atrial blanking period) and the time of the latest crossing of a nominal threshold amplitude by the motion sensor signal. The data acquired at block 304 may be acquired during each ventricular cycle over a predetermined time interval or predetermined number of ventricular cycles. For instance, control circuit 206 may acquire data from the motion sensor signal for several minutes, up to one hour or up to 24 hours for characterizing aspects of the motion sensor signal in each of one or more sensing vectors of the motion sensor. In other examples, at least N values of a motion signal feature during a respective number of N ventricular cycles are determined.

At block 306, control circuit 206 generates one or more distributions of the amplitude and/or timing data acquired at block 304. In some examples, the distribution(s) is/are generated as histogram(s). A histogram of maximum amplitude data may be generated for each available sensing vector, for example, for selecting a sensing vector or combination of vectors of the motion sensor from which atrial event sensing is performed during an atrial tracking ventricular pacing mode. Techniques for generating a distribution of motion sensor maximum amplitude data and selecting a sensing vector are described below in conjunction with FIGS. 7 and 8.

In another example, a histogram of the latest crossing time of an amplitude threshold during each ventricular cycle may be generated at block 306 for use in establishing an ending time of the A3 window (also referred to as the passive ventricular filling window). Example techniques for generating a distribution and establishing the A3 window ending time are described below in conjunction with FIGS. 9 and 10.

A distribution in the form of a histogram of maximum amplitude data may be generated at block 306 for use in establishing an early A4 sensing threshold amplitude value and a late A4 sensing threshold amplitude value of a multi-level A4 sensing threshold used for sensing A4 events during an atrial-tracking ventricular pacing mode. Techniques for generating histograms for establishing atrial event sensing threshold values are described below in conjunction with FIGS. 11-13.

At block 308, control circuit 206 analyzes one or more distributions of motion sensor signal feature data for establishing one or more atrial event sensing control parameters. Based on the distribution analysis, control circuit 206 may select an atrial event sensing parameter, which may include a motion sensor vector signal or combination of vector signals from which A4 signals are sensed during the atrial tracking pacing mode. Among other atrial event sensing parameters that may be derived from the generated distribution(s) of motion signal features are an ending time of the A3 window and the early sensing threshold amplitude and the late sensing threshold amplitude of the multi-level A4 sensing threshold. Various examples of techniques for acquiring data from the motion signal, generating distributions of the motion signal data and deriving one or more atrial event sensing parameters from the distributions are described below in conjunction with FIGS. 7-13.

Figure 7:
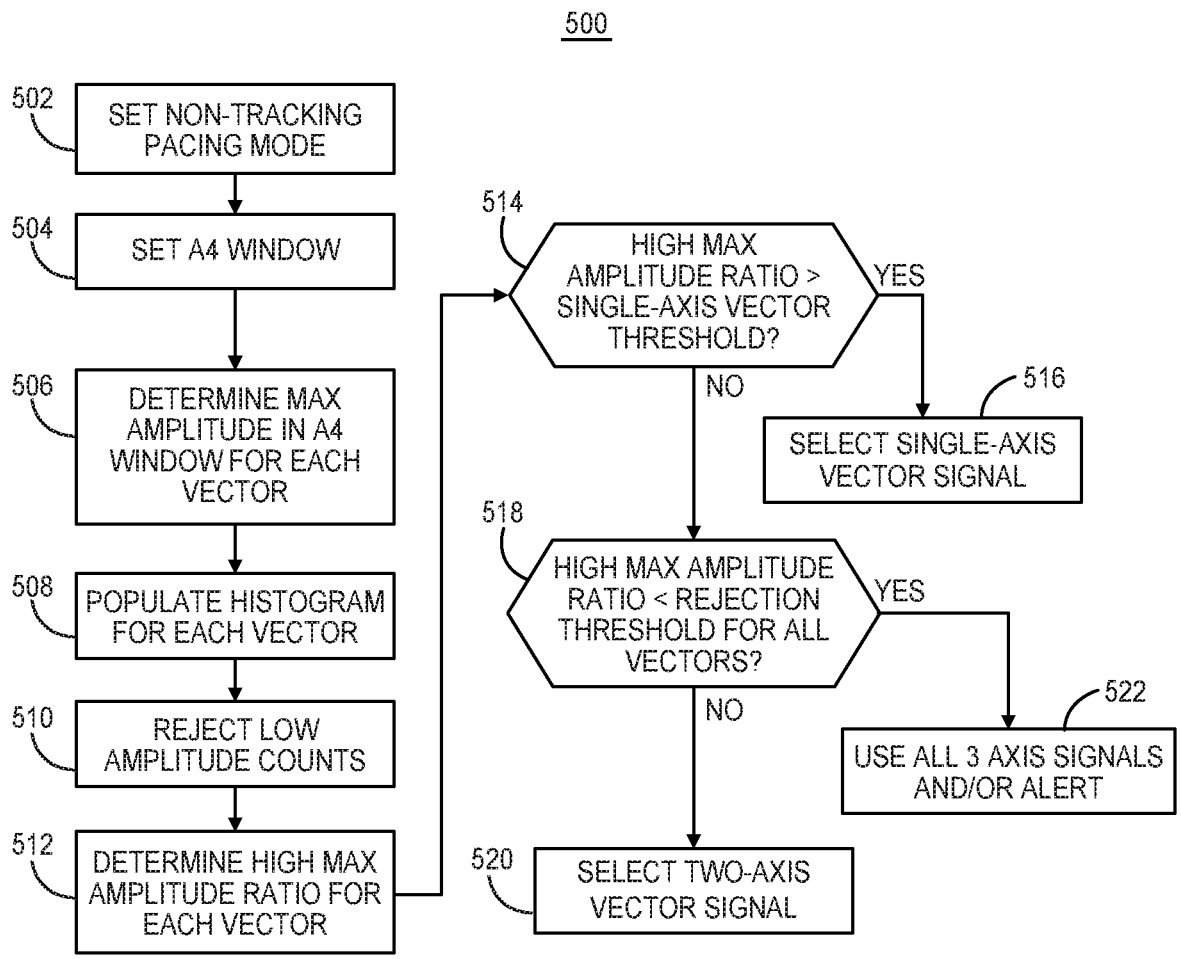
FIG. 7 is a flow chart of a method for selecting an atrial event sensing vector according to one example.

FIG. 7 is a flow chart 500 of a method for selecting an A4 sensing vector according to one example. Control circuit 206 may control the process of flow chart 500 to set an initial sensing vector during an early post-operative period after pacemaker implantation and may repeat the process to reset an A4 sensing vector selection after a specified interval of time or when A4 events are being undersensed (e.g., when threshold number of ventricular pacing pulses delivered at the rate smoothing interval during the atrial tracking ventricular pacing mode). The A4 sensing vector selection process of flow chart 500 is performed for determining which vector signal (from one axis or a combination of axes) of a multi-axis motion sensor produces a motion signal from which atrial events can be sensed most reliably, e.g., based on atrial event signal strength.

At block 502, control circuit 206 sets the pacing mode of pacemaker 14 to a non-atrial tracking ventricular pacing mode (e.g., VDI). Control circuit 206 may set the ventricular pacing interval (VV interval) according to a nominal pacing rate, e.g., 50 pulses per minute, in order to maintain a minimum, lower ventricular rate. During the asynchronous pacing mode, the A4 event may occur at varying times during the ventricular cycle. Control circuit 206 may set a nominal or default A4 window at block 504 during which the motion signal peak amplitude is detected for characterizing the motion signal. In one example, for a pacing rate of 50 pulses per minute, the A4 window may be set having a starting time at 800 to 900 ms after a delivered ventricular pacing pulse (or a sensed R-wave) and extending until the next ventricular pacing pulse (or sensed R-wave).

In other examples, the end of the A3 window and start of the A4 window may be set to a percentage of the ventricular rate interval. For example, control circuit 206 may determine the ventricular cycle length, which may be paced or sensed, for a specified number of the most recent ventricular cycles. Control circuit 206 may determine a mean or median value of the determined ventricular cycle lengths and set the A4 window to start at a percentage of the mean or median. In one example, the median ventricular cycle length of the eight most recent ventricular cycles is determined and the A3 window is set to end and the A4 window is set to start at 80% of the median ventricular cycle length or the $4^{th}$ longest ventricular cycle length out of the 8 ventricular cycles. The end of the A3 window and start of the A4 window may be set between a specified minimum and maximum time interval, e.g., not less than 650 ms and not more than 900 ms in some examples. When the specified percentage of the median ventricular cycle length falls outside the limited range, the minimum or maximum value may be used.

In some examples, setting the A4 window at block 504 may be performed by setting a long post-ventricular atrial blanking period starting from the ventricular pacing pulse. The A4 window extends from the end of the long post-ventricular atrial blanking period until the next ventricular pacing pulse. The post-ventricular atrial blanking period may be set to an extended time interval that is expected to encompass each of the A1, A2 and A3 ventricular events of the motion sensor signal, which are expected to occur at relatively predictable intervals following the ventricular pacing pulse (as shown in FIG. 5). In this way, any relatively large amplitude peak of the motion signal occurring after the extended atrial blanking period is more likely to be an A4 signal and less likely to be a ventricular event (A1, A2 or A3).

At block 506, control circuit 206 determines the maximum amplitude of the motion sensor signal during each A4 window for each motion sensor vector signal selected for analysis during the automatic sensing parameter selection process. The motion sensor vector signals selected for analysis may include one, two or all three single-axis vector signals; one, two or all three combinations of two-axis vector signals, and/or the combination of all three accelerometer axes in a three-axis vector signal. The maximum amplitude of each of the vector signals under analysis may be determined for each ventricular cycle that occurs during a predetermined time interval or over predetermined number of ventricular cycles. For example, the maximum amplitude may be determined from each vector signal during each ventricular cycle over one minute, several minutes, one hour or more or over 50 to 1000 ventricular cycles, as examples.

Control circuit 206 determines a distribution of the maximum amplitude values at block 508, e.g., by populating a histogram of maximum amplitudes determined during the A4 window for each vector signal selected for analysis. For example, a histogram of maximum amplitudes may be generated for one longitudinal vector and two radial vectors of a three dimensional accelerometer having one axis aligned with the long axis of pacemaker 14 as described above. In other examples, a histogram of maximum amplitudes may be generated for each single-axis vector signal and/or each two-axis vector signal and/or the three-axis vector signal. When a combination of two or all three axes are used to produce a vector signal, the acceleration signal sample points of the two or all three axis signals may be summed to produce a two- or three-axis vector signal. In other examples, the resultant vector signal may be determined using vector math. The maximum amplitude may be determined from rectified vector signals or may be a maximum peak-to-peak amplitude of the non-rectified vector signals.

Figure 8:
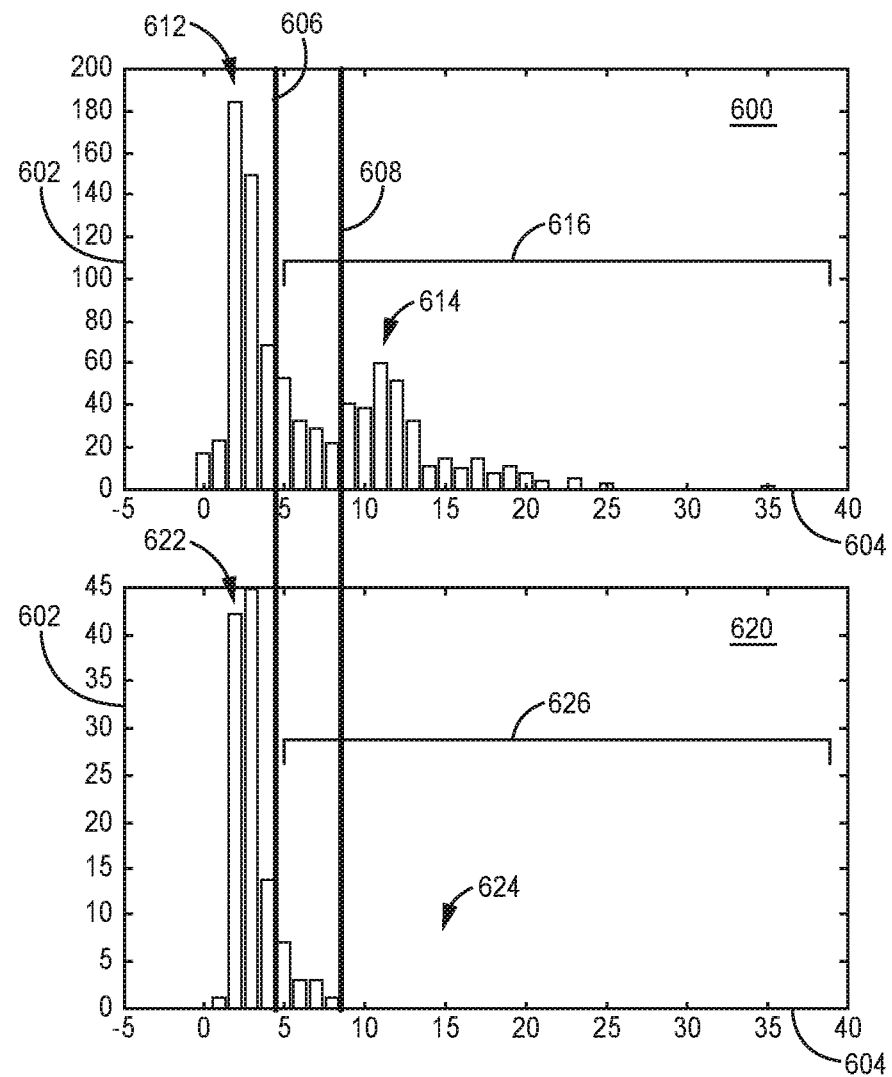
FIG. 8 depicts two example histograms generated for two different motion sensor signal vectors.

FIG. 8 depicts two example histograms 600 and 620 generated for two different motion sensor vector signals. The maximum amplitude of the vector signal detected during the A4 window is plotted along the horizontal axis 604 of each histogram 600 and 620. The horizontal axis 604 is shown in ADC units, where each ADC unit is 11.8 milli-g (acceleration of gravity), in the example shown. The histograms of amplitudes determined from the motion sensor vector signal received by the control circuit 206 from an ADC included in motion sensor 212 may be generated in ADC units, but may optionally be converted to units of acceleration, e.g., meter/second squared (m/s$^2$), for display on an external device, e.g., external device 20. For example, the acceleration conversion ratio may be 1 m/s$^2$ per 100 milli-g.

The maximum amplitude during each A4 window is matched to a histogram bin value or range. The matching histogram bin count is increased by one for each matching maximum amplitude value to track the frequency of occurrence of each maximum amplitude value or range. The frequency or count of binned maximum amplitude values obtained over the predetermined time interval for the given vector signal is plotted along the y-axis 602 in each histogram. Since the ventricular cycles are asynchronous with the atrial rhythm, numerous ventricular cycles may occur during which no true A4 event occurs during the A4 window. Thus, relatively high counts 612 and 622 of relatively low maximum amplitudes may occur when atrial systole does not happen to coincide with the nominal A4 window. A low maximum amplitude may be defined as a maximum amplitude detected during the A4 window that is less than 5 ADC units in this example. The high frequency of A4 windows having a relatively low maximum amplitude of the vector signal reflects the relatively large number of ventricular cycles during which atrial systole does not happen to coincide with the A4 window.

A reliable sensing vector signal includes relatively high counts 614 at relatively high maximum amplitude values, e.g., in the range of 7 to 15 ADC units, as shown in the example histogram 600. The moderately high frequency (counts 614) of high maximum amplitude (e.g., 8 ADC units or more) during the A4 window indicates the occurrence of A4 signals that happen to coincide with the A4 window during the non-atrial tracking pacing mode. Since these A4 signals have a relatively high amplitude, the vector signal used to generate histogram 600 may be a highly reliable vector signal for sensing atrial events.

In comparison, the example histogram 620 shows a relatively low or zero count 624 of relatively high maximum amplitude signals during the A4 window. The vector signal used to produce histogram 620 is considered to be unreliable for use in detecting atrial events since most or all of the maximum amplitudes during the A4 window are relatively low, e.g., within the range of the baseline noise of the vector signal. This means that even on cycles that the A4 signal coincides with the A4 window, the A4 amplitude is substantially in the range of the baseline noise of the vector signal, e.g., less than 5 ADC units. The orientation of the axis or axes used to produce the vector signal associated with histogram 620 may result in a null signal during atrial systole.

Referring again to FIG. 7 with continued reference to FIG. 8, at block 510, the histogram bins corresponding to relatively low maximum amplitudes may be rejected as being low level noise in the vector signal. In the example of FIG. 8, histogram bins storing counts of maximum amplitudes that are less than a noise threshold 606, e.g., 5 ADC units, may be discarded as noise. The noise threshold 606 may be set to a value greater than or less than 5 ADC units in other examples and may be set according to the baseline noise of the vector signal. In some examples, the noise threshold 606 is optional or the noise threshold may be set to zero.

At block 512, control circuit 206 may determine whether the maximum amplitudes meet vector selection criteria for each vector signal tested. In one example, the total number of maximum amplitudes that are greater than the noise threshold 606 (e.g., all maximum amplitudes counted over the range 616 and 626 in histograms 600 and 620, respectively), is determined by control circuit 206 at block 512. The number of high maximum amplitudes that are greater than a high amplitude threshold 608 is also determined at block 512 by control circuit 206. The high amplitude threshold 608 is set to 8 ADC units in the example shown. The number of maximum amplitudes greater than 8 ADC units is determined as the high maximum amplitude count. The ratio of the high maximum amplitude count to the count of all maximum amplitudes greater than the noise threshold 606 is determined at block 512 as the high maximum amplitude ratio. This high maximum amplitude ratio is determined for each of the tested A4 sensing vector signals and is an indication of the frequency of high amplitude signals (as generally depicted by 614 in FIG. 8) that occur during the A4 window and are highly likely to be actual A4 signals since they are occurring outside the post-ventricular atrial blanking period.

Control circuit 206 may compare this high maximum amplitude ratio of the number of high maximum amplitudes (greater than threshold 608) to the number of all maximum amplitudes greater than the noise threshold 606 determined for each single-axis vector signal that is analyzed to a single-axis vector selection threshold at block 514. In one example, if at least 50% of the maximum amplitude values are greater than the high amplitude threshold, after rejecting the low maximum amplitude values that are less than the noise threshold, the single-axis vector signal may be selected as the A4 sensing vector and may be used as a single-axis vector signal for reliable A4 sensing. In the example histogram 600 of FIG. 8, more than 50% of the maximum amplitudes acquired over the range 616 (greater than 4 ADC units) are greater than 8 ADC units, the high amplitude threshold 608. As such, when this vector signal is a single-axis vector signal that was used to obtain the maximum amplitude data for generating histogram 600, this single-axis vector signal may be selected as the A4 event sensing vector signal at block 516. Use of a single-axis sensing vector signal for sensing A4 events allows a single axis of the accelerometer to be powered for generating the A4 sensing vector signal, which saves power and may extend the functional life of pacemaker 14 compared to using a combination of two or more axes for generating a vector signal for sensing atrial events.

In instances where two or more single-axis vector signals meet the criteria applied at block 514, the single-axis vector signal having the highest high maximum amplitude ratio may be selected as a single-axis A4 sensing vector signal at block 516. In general, control circuit 206 may select a vector signal that produces a distribution of the maximum amplitudes during the A4 window that is skewed right (with a distribution tail longer on the right than on the left when amplitude is increasing from left to right on the x-axis). A vector signal having a greatest median maximum amplitude, a highest rightward skew of the maximum amplitude distribution, or other metric indicting a rightward skew of the maximum amplitude distribution may be selected as the sole vector signal at block 516 to be used for sensing A4 events during an atrial tracking ventricular pacing mode.

In some examples, the maximum amplitudes determined for each vector signal may be compared to rejection criteria. When the maximum amplitudes for all vector signals meet rejection criteria, an alert may be generated. For instance, if the high maximum amplitude ratio (the ratio of the number of maximum amplitudes that are greater than the high amplitude threshold 608 to the number of maximum amplitudes greater than the noise threshold 606) is less than a rejection threshold, as determined at block 518, control circuit 206 may select a combination of all three axis signals for producing the A4 sensing vector signal at block 522 or select the best combination of two out of the three axis signals for generating a two-axis vector signal for A4 sensing. Selecting the minimum number of accelerometer axes required to sense A4 events may conserve current demand from power source 214. Additionally or alternatively, an alert may be generated to notify the clinician that none of the vector signals analyzed have met criteria for reliable A4 sensing. The notification may be transmitted by telemetry circuit 208 to external device 20 at block 522.

In some instances, all three single-axis vector signals may have a high maximum amplitude ratio that is less than the single-axis vector signal threshold ("no" branch of block 514), but at least one, two or all three single-axis vector signals may have a high maximum amplitude ratio that is greater than the rejection threshold ("no" branch of block 518). When at least one out of the possible single-axis vector signals has a high maximum amplitude ratio that is between the single-axis vector threshold and the rejection threshold, control circuit 206 may select two axis signals (corresponding to two different motion sensor axes) at block 520 to be used in combination for A4 event sensing. The two single-axis vector signals having the highest high maximum amplitude ratios may be selected to be used in combination for sensing atrial events. These two single-axis vector signals may be summed to produce a two axis vector signal. In some examples, the single axis vector signal that is aligned with the longitudinal axis of the housing 150 of pacemaker 14 is selected with one other vector, e.g., a radial vector. The atrial event sensing vector may be selected as a combination of the longitudinal single-axis vector signal summed with one of the radial single-axis vector signals having the highest high maximum amplitude ratio determined at block 512 to produce a two-axis vector signal for A4 event sensing.

When two (or three) single-axis vector signals are selected in combination as the A4 event sensing vector signal the multi-axis vector signal may be determined by vector summation of the two (or three) individual vector signals. The vector signals may be summed digitally using the digitized, rectified vector signals. Summation may be performed after rectification to avoid destructive summation of two or more vector signals. In other examples, two or three individual analog vector signals may be summed when a single-axis vector signal does not produce a high maximum amplitude ratio greater than the single-axis vector threshold.

In other examples, instead of determining a ratio as indicated t block 512, another metric of the distribution of maximum amplitudes may be determined and compared to vector selection and/or rejection criteria. For example, as described below in conjunction with FIG. 15, the median, mean or a specified percentile of all maximum amplitudes determined at block 506 may be determined (after discarding maximum amplitudes less than a noise threshold in some examples). The median of maximum amplitudes (or other metric of the distributions) determined for each of the vector signals being analyzed may be compared to each other, and the vector signal producing the greatest median maximum amplitude may be selected. In some examples, a single-axis vector signal may be selected when it corresponds to the greatest median maximum amplitude. However, a vector signal that is a combination of at least two axis signals will generally have a greater median maximum amplitude than a single-axis vector signal (due to the summation of two single-axis signals). As such, in some examples, a two-axis vector signal that has the greatest median maximum amplitude may be selected as the atrial event sensing vector signal.

In instances where each of the two-axis vector signals are rejected due to the maximum amplitudes meeting rejection criteria, the combination of all three motion sensor axis signals may be selected as a three-axis vector signal for atrial event sensing. As further described in conjunction with FIG. 15, a two-axis vector signal (or any analyzed vector signal) may be rejected when fewer than a threshold count of the maximum amplitudes acquired for the given vector signal are greater than a minimum amplitude threshold. The minimum amplitude threshold may be set to the minimum available A4 sensing threshold amplitude in some examples.

Figure 9:
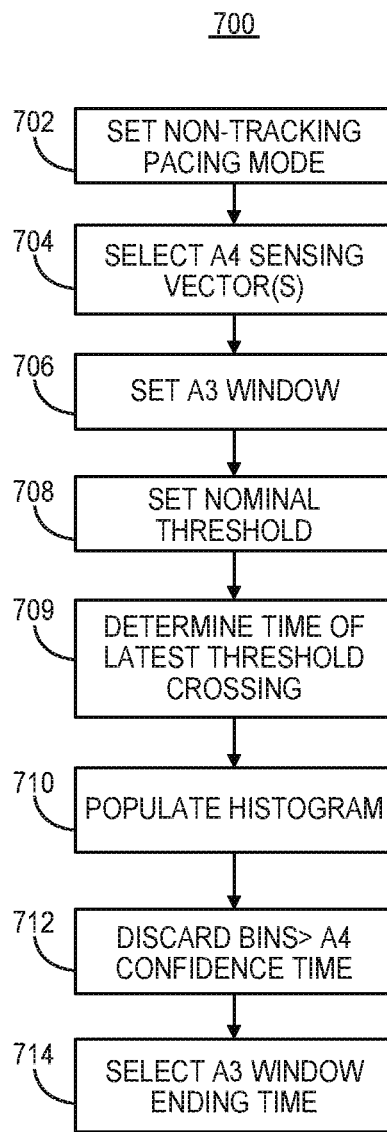
FIG. 9 is a flow chart of a method for establishing an ending time of a passive ventricular filling window, also referred to herein as an "A3 window."

FIG. 9 is a flow chart 700 of a method for establishing an ending time of the A3 window (e.g., ending time 422 of window 424 shown in FIG. 5). At block 702, control circuit 206 sets the pacing mode to the non-atrial tracking pacing mode. The pacing rate may be set to a nominal pacing rate, e.g., 50 pulses per minute, by setting the VV pacing interval. At block 704, the A4 sensing vector (a single-axis vector signal or a summation of two or more single-axis vector signals) is selected. Control circuit 206 may select the vector signal established as the A4 sensing vector in the process described above in conjunction with FIGS. 7 and 8. The process of flow chart 700 may be performed only for a selected atrial event sensing vector signal (a single-axis vector or a two-axis or three-axis vector signal from the summed combination of two or more single-axis vector signals) and may be repeated if the A4 sensing vector signal selection is changed. In other examples, at least portions of the process of flow chart 700 may be performed for all available motion sensor vector signals or multiple selected vector signals to enable simultaneous motion sensor signal data acquisition for use in generating distributions of motion sensor signal features.

In some examples, the non-atrial tracking pacing mode and rate are still in effect after selecting the atrial event sensing vector at block 520 of FIG. 7. Control circuit 206 may advance directly to the process of flow chart 700 for establishing the A3 window ending time, e.g., directly from block 520 of FIG. 7 to block 706 of FIG. 9. In examples that include a one-dimensional, single-axis motion sensor or a fixed A4 sensing vector signal selection, the vector selection process of FIG. 7 is unnecessary. The process of establishing the A3 window ending time according to flow chart 700 may be performed without performing the process of flow chart 500 first by selecting a manually programmed or default atrial event sensing vector signal at block 704.

A nominal A3 window is set at block 706, e.g., beginning 600 ms after a ventricular event, sensed or paced, and extending until the next ventricular event. The nominal A3 window may be set by setting a post-ventricular atrial blanking period extending from a ventricular electrical event, sensed or paced, for a predetermined time interval, e.g., 600 ms. The nominal A3 window may be set to begin after an expected time of the A1 and A2 signals (e.g., as shown in FIG. 4) and extend as late as the next ventricular electrical event to increase the likelihood of capturing A3 signals during the nominal A3 window. In some examples, the A3 window is set at block 706 to start at a fixed interval, e.g., 600 ms after a ventricular event (sensed R-wave or ventricular pacing pulse) and extend to an A3 window ending time set to a percentage, e.g., 80%, of a mean or median ventricular cycle length determined from a specified number of recent ventricular cycle lengths, e.g., the 8 ventricular cycle lengths.

At block 708, control circuit 206 sets a nominal threshold amplitude. The nominal threshold amplitude may be 9 ADC units, which may correspond to 0.9 m/s$^2$, as one example. The timing of the latest crossing of the nominal threshold amplitude in each A3 window is determined at block 709 over a predetermined time period or number of ventricular cycles for each vector signal under analysis. When atrial systole (and the A4 event) does not happen to occur during the A3 window, the latest threshold crossing may be a true A3 signal and is expected to occur relatively early in the nominal A3 window since A3 signals are ventricular event signals that follow the ventricular electrical event at a relatively consistent time interval. When atrial systole does happen to occur during the A3 window, the latest threshold crossing could be an A3 or an A4 signal, depending on when atrial systole occurs during the A3 window. Relatively late threshold crossings during an extended A3 window, however, are much more likely to be an A4 signal than an A3 signal, since the A3 signal is generally tied to the timing of the ventricular electrical event. In some ventricular cycles, the motion sensor vector signal may cross the nominal threshold amplitude more than once during the A3 window. For example, the true A3 signal and the true A4 signal may cross the nominal threshold amplitude. In this case, the timing of only the latest threshold crossing is stored in some examples.

When the threshold amplitude crossings are accumulated over a large number of ventricular cycles, e.g., over at least 50 to 100 ventricular cycles or more, a relatively high frequency of the latest threshold crossings will represent A3 signals and some will represent A4 signals when atrial systole happens to occur during the A3 window. In some instances, fused A3/A4 events may occur during the A3 window as the latest threshold amplitude crossing. A relatively late threshold amplitude crossing could be an A1 signal in some instances, although A1 and A2 signals are likely to occur during the post-ventricular atrial blanking period. A distribution of the timing of the latest threshold amplitude crossings may reveal an expected time of A3 events and an expected time of A4 events during the ventricular cycle.

The data accumulated at block 709 may be used to populate a histogram at block 710. The latest nominal threshold amplitude crossing times accumulated beat-by-beat over the predetermined time interval or number of ventricular cycles may be binned according to histogram bin time interval ranges. A count of the number of latest threshold crossings occurring during each bin time interval range is determined.

Figure 10:
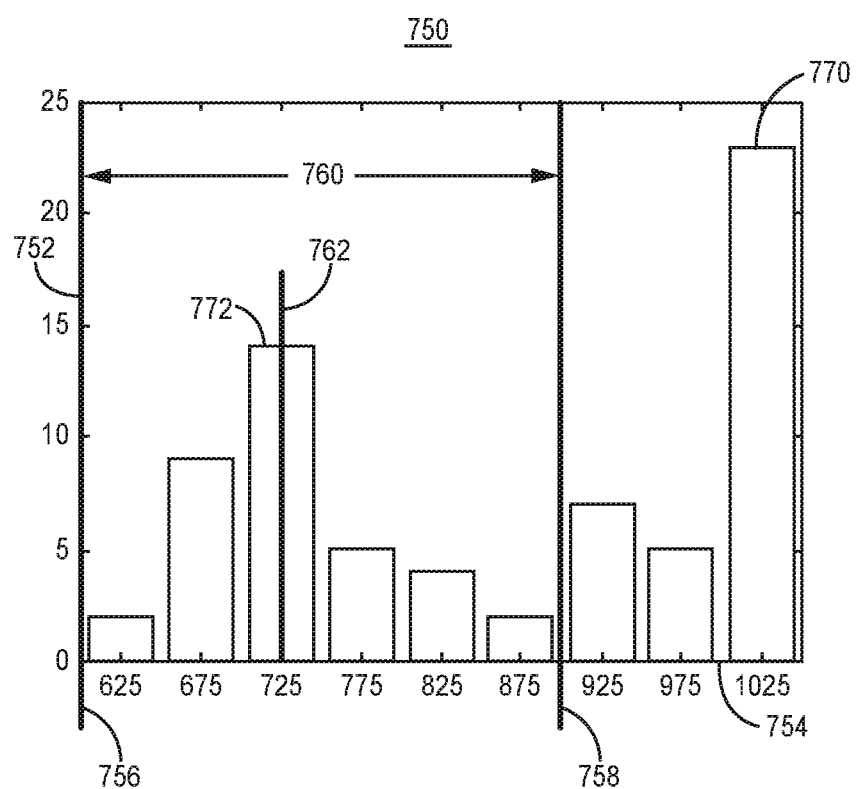
FIG. 10 is an example of a histogram of the latest threshold amplitude crossing times during an extended A3 window.

FIG. 10 is an example of a histogram 750 of the latest nominal threshold amplitude crossing times that may be generated at block 710 of FIG. 9 for one sensing vector signal. The latest threshold crossing time is plotted along the x-axis 754 in units of milliseconds (ms) and represents the time after the ventricular electrical event that the last nominal threshold amplitude crossing occurred during a ventricular cycle. The frequency or count of latest threshold crossing times is plotted along the y-axis 752. In the example shown the left-most, lowest bin includes the latest crossing times occurring in the range of 601 ms to 650 ms after the ventricular electrical event for an A3 window having a starting time 756 at 600 ms after the ventricular electrical event. The right-most bin includes the latest crossing times occurring in the range of 1001 to 1050 ms after the ventricular electrical event (pacing pulse or sensed R-wave). Each bin includes a time range of 50 ms in this example, and the A3 window extends from 600 ms after the preceding ventricular electrical event to the next ventricular electrical event. Other starting and/or ending times for the A3 window may be selected (and may depend on the ventricular rate), and other time ranges for the histogram bins may be used in other examples.

The distribution represented by histogram 750 presents a bimodal distribution having a left peak 772 corresponding to probable A3 signals during the extended A3 window and a right peak 770 corresponding to probable A4 signals during the extended A3 window. An A4 confidence time threshold 758 may be set as a time after which the nominal threshold amplitude crossings are expected to be A4 signals with a high probability and highly unlikely to be A3 signals. In the example of FIG. 10, the A4 confidence time threshold 758 is set to 900 ms based on the ventricular pacing rate being set to 50 pulses per minute. The A4 confidence time threshold 758 may be set to a fixed value based on the ventricular rate during the accumulation of the latest threshold crossing times. In other examples, the A4 confidence time threshold 758 may be set based on a predetermined percentage, e.g., a predetermined percentile, of all of the accumulated latest threshold crossing times.

The leftmost peak of the bimodal distribution is represented by the highest bin count 772 over the remaining range 760 of histogram bins after discarding bins higher than the A4 confidence time threshold 758. The leftmost peak 772 likely represents the occurrence of A3 events during the extended A3 window and may include some fused A3/A4 signals. An appropriate ending time for the A3 window may be any time from the median value 762 of the latest threshold crossing times over the range 760 up to the A4 confidence time threshold 758. An A3 window ending time may be selected between the median 762 and the A4 confidence time threshold 758 so that the A3 window includes A3 signals (and fused A3/A4 signals) with a high probability. In some examples, the A3 window ending time, or the A4 window starting time, used for A4 sensing during the atrial tracking ventricular pacing mode may be set to a time based on the left peak of the bimodal distribution of the latest nominal threshold crossing times. For instance, the A3 window ending time used during an atrial tracking ventricular pacing mode may be set to the left peak (when time is increasing from left to right) of the bimodal distribution plus an offset, where the offset is a predetermined value ranging from zero to 200 ms as examples.

Returning to FIG. 9, the counts in the populated histogram bins greater than the A4 confidence time threshold are discarded at block 712. At block 714, control circuit 206 selects the A3 window ending time based on the remaining histogram bin data after discarding the bins greater than the A4 confidence time threshold. Control circuit 206 may determine the median time of the latest nominal amplitude threshold crossing of the remaining bins. The A3 window ending time may be established as the median of the distribution plus an offset. The offset may be a predetermined value ranging from 0 ms to 200 ms, e.g., 50 ms to 100 ms. In other examples, the A3 window ending time may be set to a percentile of the remaining histogram bin counts (over range 760 in FIG. 10) after discarding histogram bins greater than the A4 confidence time threshold. For instance, after discarding the bin counts greater than the A4 confidence time threshold 758, the A3 window ending time may be set to the time at which at least 70%, 80%, 90%, or 95% of the latest threshold crossing times are less than the A3 ending time.

In the example of FIG. 10, the A3 window starts at the expiration of a post-atrial ventricular blanking period, e.g., 600 ms after a ventricular event, until the next ventricular event (pacing pulse or sensed R-wave). During this extended A3 window, both early and late threshold crossings are detected, resulting in the bimodal distribution shown in FIG. 10 which includes a left peak 772 corresponding to likely A3 event signals and a right peak 770 corresponding to likely A4 event signals. Rather than setting an extended A3 window then discarding the bins greater than the A4 confidence time threshold, the A3 window may be set at block 706 to extend from 600 ms (or the end of the post-ventricular atrial blanking interval) until the A4 confidence time threshold 758, which may be set to a percentage of the median ventricular cycle length as described above. For instance, the A3 window may be set to extend from 600 ms until 80% of the median of eight ventricular cycle lengths, and not less than 650 ms or greater than 900 ms when the pacing lower rate is set to 50 pulses per minute. In this way, the latest threshold crossings during the A3 window are most likely A3 events since they occur before the A4 confidence time threshold 758. The histogram bins corresponding to even later threshold crossings, after the A4 confidence time threshold 758, need not be populated since they are unlikely to contain true A3 event threshold crossing times. The A3 window ending time may be established as the median of the distribution of latest threshold crossing times plus an offset.

Figure 11:
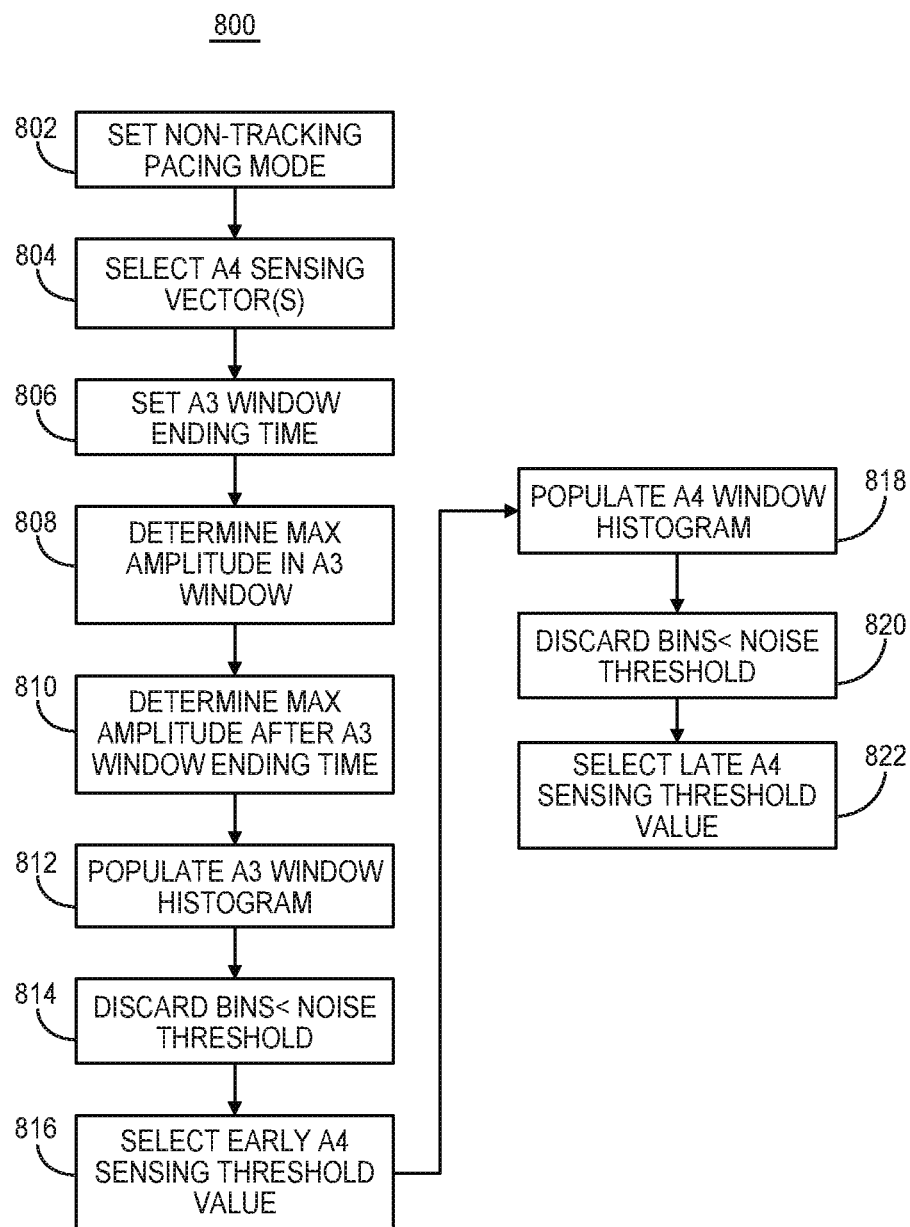
FIG. 11 is a flow chart of a method for establishing early and late values of the atrial event sensing threshold amplitude to be applied during and after the passive ventricular filling window, respectfully.

FIG. 11 is a flow chart 800 of a method for establishing early and late values for the A4 sensing threshold to be applied during the A3 window and after the A3 window, respectfully, e.g. for sensing A4 signals during an atrial-tracking ventricular pacing mode. At block 802, control circuit 206 sets the pacing mode to the non-atrial tracking pacing mode and sets the VV pacing interval according to a selected pacing rate, e.g., 50 pulses per minute. At block 804, control circuit 206 selects the A4 sensing vector (as a single-axis vector signal or combination of two or more acceleration axis signals), e.g., based on the method of FIG. 7.

In some examples, the process of flow chart 800 is performed using only the A4 sensing vector signal selected by the method of FIG. 7. In other examples, portions of the process of flow chart 800 may be performed for all available motion sensor vector signals, including single-axis, two-axis and three-axis vector signals, or any number of vector signals selected to be analyzed. For example, the data required to generate histograms for setting the A4 sensing threshold amplitude values may be acquired for multiple vector signals used in the process of FIG. 7, but the data corresponding only to the vector signal selected as the A4 sensing vector signal at block 516, 520 or 522 of FIG. 7 may be used in setting the A4 sensing threshold amplitude values.

The A3 window ending time may be set at block 806. In one example, the A3 window ending time is set to a percentage of a median ventricular cycle length as described above. In other examples, the A3 window is set to the A3 window ending time selected at block 714 of FIG. 9, based on the histogram of the latest threshold crossing times. The A3 window may extend from a fixed starting time, which may be programmable or based on empirical data, to the A3 window ending time that is automatically determined from a distribution of latest nominal threshold amplitude crossing times as described above in conjunction with FIGS. 9 and 10. In other examples, a manually programmed or default A4 sensing vector signal and/or A3 window ending time are set at blocks 804 and 806, respectfully. In this case, the processes of FIGS. 7 and 9 are not necessarily performed prior to the process of FIG. 11 for establishing A4 sensing threshold amplitude values.

At block 808, control circuit 206 determines the maximum amplitude of the motion signal during the A3 window for each ventricular cycle over a predetermined number of cycles or predetermined time interval. Control circuit 206 determines the maximum amplitude of the motion signal after the A3 window ending time and before the next ventricular electrical event (e.g., during the A4 window) at block 810, for each ventricular cycle over the predetermined number of cycles or predetermined time interval.

The maximum amplitudes determined during the A3 windows are used by control circuit 206 to generate an A3 window maximum amplitude distribution, for example by populating an A3 window maximum amplitude histogram, at block 812. The counts of histogram bins corresponding to maximum amplitudes less than a noise threshold may be discarded at block 814. A very low maximum amplitude during the A3 window may not be representative of a true A3 or A4 event and may be baseline noise of the motion signal. At block 816, control circuit 206 selects an early A4 sensing threshold amplitude value to be applied during the A3 sensing window based on the remaining, non-discarded histogram data. Methods for selecting the early A4 sensing threshold amplitude value based on the A3 window histogram data are described below in conjunction with FIG. 12.

Control circuit 206 may generate a distribution of the A4 window maximum amplitude data, e.g., by populating an A4 window maximum amplitude histogram, at block 818 using the maximum amplitudes determined at block 810 during the A4 window (after the A3 window until the end of the ventricular cycle marked by the next ventricular electrical event). Histogram bins storing maximum amplitudes that are less than a noise threshold are discarded at block 820. Control circuit 206 selects a late A4 sensing threshold amplitude value based on the remaining (non-discarded) distribution of maximum amplitude values at block 822. Methods for selecting the late A4 sensing threshold amplitude value based on the histogram data are described below in conjunction with FIG. 13.

Figure 12:
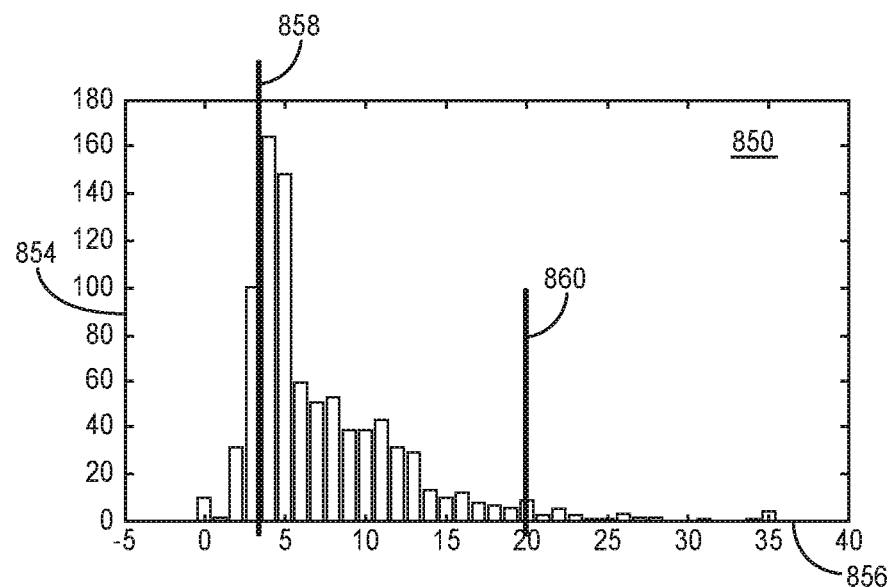
FIG. 12 is one example of a histogram of motion signal maximum amplitudes used for establishing an early atrial event sensing threshold amplitude.

FIG. 12 is one example of a histogram 850 of maximum amplitudes of a motion sensor vector signal during A3 windows that may be generated by control circuit 206. The maximum vector signal amplitude is plotted on the x-axis 856 (in ADC units in this example). The counts of each histogram bin are plotted along the y-axis 854. Each histogram bin is shown to include an amplitude range of one ADC unit in FIG. 12 though other histogram bin resolutions may be used (and may be arranged in units of g or $m/s^2$). Each bin stores the count of how many times the maximum amplitude of the vector signal during the A3 window falls in the respective bin range.

A noise threshold amplitude 858 may be a predefined value or determined as a percentile of the histogram frequency distribution. Maximum amplitudes during the A3 window that are less than the noise threshold amplitude 858 may be attributed to baseline noise during the A3 window (or very low amplitude A3 signals). The histogram bins corresponding to maximum amplitudes that are less than the noise threshold amplitude 858 may be discarded for the purposes of selecting an early A4 sensing threshold amplitude, also referred to herein as an "early atrial event sensing threshold." In the example of FIG. 12, the noise threshold may be 4 ADC units, or about 50 milli-g or about 0.5 m/s$^2$.

After discarding the histogram bins that are less than (to the left of) the noise threshold amplitude 858, control circuit 206 may determine the early A4 sensing threshold value 860 as a percentile of the remaining distribution of maximum amplitudes determined during the A3 windows. Since most of the maximum amplitude values determined during the A3 windows and counted in the histogram 850 are expected to represent actual A3 events, a majority of the maximum amplitudes should be less than the early A4 sensing threshold value 860 so that they are not falsely detected as A4 events.

A smaller percentage of the relatively high maximum amplitudes occurring during the A3 window, e.g., those greater than the early A4 sensing threshold value 860 may represent fused A3/A4 events, which should be sensed as A4 events. The early A4 sensing threshold value 860 may be set to a relatively high percentile, e.g., the eightieth, eighty-fifth, or ninetieth percentile of the remaining (non-discarded) maximum amplitudes of histogram 850 according to one example. In one example, the upper 15% of the maximum amplitude signals during the A3 window (after discarding bins below the noise threshold) would meet atrial event sensing criteria and would be sensed as A4 signals, e.g., during an atrial tracking pacing mode. The lower 85% of the maximum amplitude signals during the A3 window would not be sensed as A4 signals.

Figure 13:
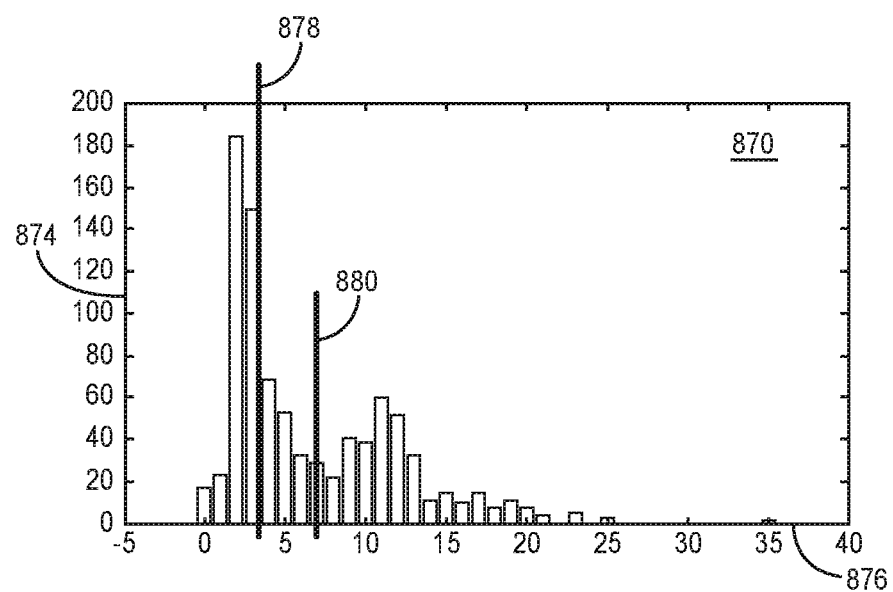
FIG. 13 is one example of a histogram of motion signal maximum amplitudes for establishing a late atrial event sensing threshold amplitude.

FIG. 13 is one example of an A4 window maximum amplitude histogram 870 that may be produced by control circuit 206 at block 818 of FIG. 11 for one vector signal being analyzed. The maximum amplitude during the A4 window of the vector signal being analyzed is plotted on the x-axis 876. The counts of each histogram bin are plotted along the y-axis 874. Each histogram bin is shown to include a range of one ADC unit in FIG. 13 though other histogram bin resolutions may be used. Each bin stores the count of how many times the maximum amplitude of the vector signal after the A3 window (during the A4 window) falls in the respective bin range.

A noise threshold amplitude 878 may be a predefined value or determined as a percentile of the histogram frequency distribution. The histogram bin counts less than the noise threshold amplitude 878 may be discarded for the purposes of selecting a late A4 sensing threshold amplitude value. These relatively low maximum amplitude signals during the A4 window are likely baseline noise and not true A4 signals. In the example of FIG. 13, the noise threshold is 5 ADC units (or about 0.6 m/s$^2$). Counts in bins less than 5 ADC units are discarded for the purposes of selecting a late A4 sensing threshold amplitude value, also referred to herein as a "late atrial event sensing threshold."

After discarding the histogram bins corresponding to maximum amplitudes that are less than the noise threshold amplitude 878, control circuit 206 may determine the late A4 sensing threshold amplitude value 880 as a percentile of the remaining maximum amplitude distribution. Since most of the maximum amplitude values determined during the A4 window and counted in the histogram 870 are expected to represent actual A4 signals, a majority of the maximum amplitudes should be greater than the late A4 sensing threshold value 880 to avoid undersensing of the A4 events. A smaller percentage of the maximum amplitudes occurring during the A4 window may be noise or even late A3 signals. The late A4 sensing threshold value 880 may be set to a relatively low percentile of the remaining (non-discarded) maximum amplitudes of histogram 870, e.g., the fifth percentile. In this way, after discarding maximum amplitudes less than the noise threshold 878, the lower 5% of the remaining maximum amplitude signals during the A4 window would not be sensed, but 95% of the maximum amplitude signals would be greater than the late A4 sensing threshold value 880 and meet atrial event sensing criteria, e.g., during an atrial tracking ventricular pacing mode. The example percentiles and noise thresholds given here are illustrative in nature and it is to be understood that other percentiles and noise thresholds may be used to establish the early and late A4 sensing threshold values.

The histograms generally depicted in the drawings presented herein, or other types of graphical representations, of the distributions of motion sensor signal features determined for use in setting atrial event sensing parameters may be generated for display on display unit 54 of external device 20. The generated display may include the value or a graphical depiction (e.g., a line, bar or icon overlaid on the histogram) to indicate the atrial event sensing parameter value or setting determined by control circuit 206 (or external processor 52) based on the distribution of the determined features.

Figure 14:
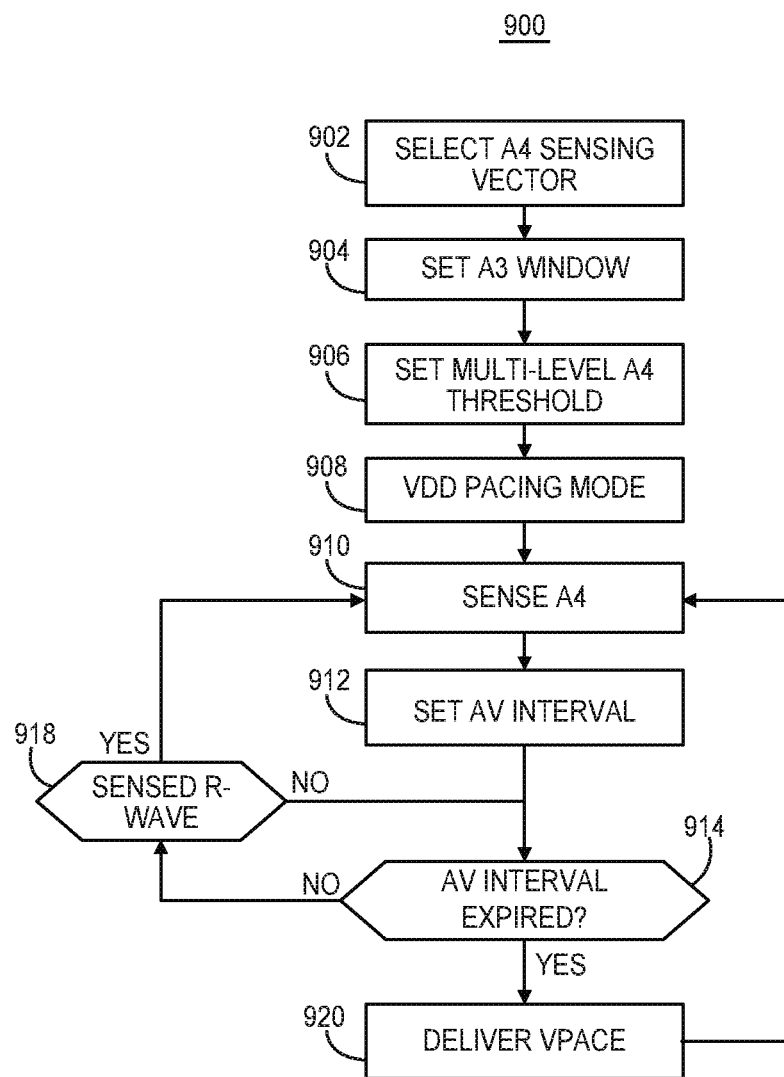
FIG. 14 is a flow chart of a method for controlling atrial-synchronized ventricular pacing according to one example.

FIG. 14 is a flow chart 900 of a method for controlling atrial-synchronized ventricular pacing according to one example. At block 902, control circuit 206 selects an A4 sensing vector. The A4 sensing vector (a single-axis vector signal, two-axis vector signal or three-axis vector signal) may be selected using the methods described above in conjunction with FIGS. 7 and 8. At block 904, the A3 window is set according to a starting time and an ending time. The ending time may be set to a time following a preceding ventricular electrical event that is determined using the method described above in conjunction with FIGS. 9 and 10. At block 906, the multi-level A4 sensing threshold is set by establishing the early A4 sensing threshold amplitude value and the late A4 sensing threshold amplitude value using the methods described in conjunction with FIGS. 11-13.

At least one of the atrial sensing parameters out of the A4 sensing vector, A3 window ending time, early A4 sensing threshold amplitude value and/or late A4 sensing threshold amplitude value is established by determining features of the motion sensor signal, generating at least one histogram or other representation(s) of the distribution of determined feature(s) of the motion sensor signal and selecting the respective A4 sensing parameter based on an analysis of the distribution. In some examples, one or more of the atrial event sensing parameters including the A4 sensing vector, A3 window ending time and early and late A4 sensing threshold values may be set to a default or user programmable value without generating a histogram or other representative distribution of motion signal features.

In some examples, the A4 sensing vector is determined first as shown by block 902. After the A4 sensing vector is selected, an A3 window ending time may be established (block 904), followed by the early and late A4 sensing threshold amplitude values (block 906). In other examples, however, A4 sensing parameters may be determined in a different sequence than that shown in in FIG. 14 or determined partially or wholly concurrently. For instance, a nominal A3 window ending time of 800 to 900 ms may be set while pacing in a non-atrial tracking pacing mode to enable data acquisition simultaneously during multiple ventricular pacing cycles for generating distributions of motion sensor signal data for generating two or more atrial event sensing parameters simultaneously. The maximum amplitude during the A3 window, the maximum amplitude after the A3 window, and the latest nominal threshold crossing occurring after the start of the A3 window (e.g. after 600 ms) may be determined from each ventricular cycle for generating distributions such as the histograms shown in the accompanying drawings. The A4 sensing vector, A3 window ending time, and early and late values of the atrial event sensing threshold values may be established based on concurrently acquired motion sensor signal features and respective distributions generated therefrom.

At block 908, control circuit 206 may set the pacing mode to an atrial tracking ventricular pacing mode such as a VDD pacing mode. At block 910, atrial event detector circuit 240 senses an A4 event during a ventricular cycle using the A4 sensing parameters established at blocks 902 through 906. Control circuit 206 may generate an atrial sensed event signal in response to the atrial event detector circuit 240 sensing the A4 event. The atrial sensed event signal may be used for controlling the timing of ventricular pacing pulses during the VDD pacing mode. The atrial tracking ventricular pacing mode that is set at block 908 may be referred to as an atrial synchronized ventricular pacing mode because an AV pacing interval may be started (block 912) in response to sensing an A4 signal (block 910) for controlling the timing of ventricular pacing pulses. If an R-wave is sensed before the AV interval expires ("yes" branch of block 918), control circuit 206 senses the next A4 signal at block 910. An A4 signal is sensed in response to the earliest crossing of the multi-level atrial event sensing threshold during the A3 window or the A4 window.

Upon expiration of the AV pacing interval ("yes" branch of block 914), a ventricular pacing pulse is generated by the pulse generator 202 and delivered (block 920). In this way, the ventricular pacing pulses are synchronized to atrial systolic events to provide a more normal heart rhythm in a patient experiencing AV conduction block.

Figure 15:
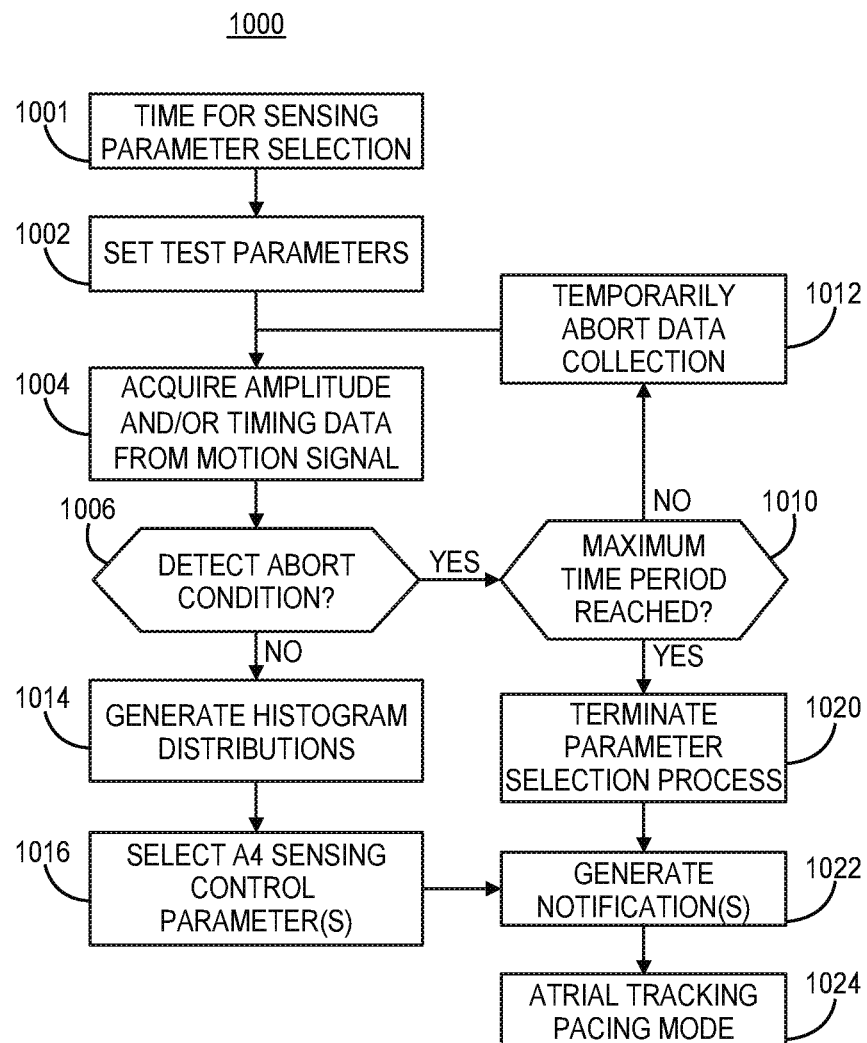
FIG. 15 is a flow chart of a process performed by a pacemaker for setting atrial event sensing parameters according to another example.

FIG. 15 is a flow chart 1000 of a process performed by pacemaker 14 for setting atrial event sensing parameters according to another example. The automatic selection of starting values for atrial event sensing parameters may be initiated by control circuit 206 at block 1001 after a time delay following a telemetry session with external device 20 in some examples. For instance, the feature of automatic selection of atrial event sensing parameters may be programmed "on" or enabled by a user interacting with external device 20 during an implant procedure or any patient follow-up procedure, in a clinic or hospital or remotely. The control circuit 206 may detect inactivity or termination of a telemetry session with external device 20 and initiate the automatic selection process at block 1001 by waiting for a time delay, e.g., after one to ten minutes or after three minutes in one example, after telemetry communication is no longer received by pacemaker telemetry circuit 208. This time delay after receiving of a telemetry communication signal has stopped may allow other programming or procedures to be completed, e.g., during an implant procedure or programming and interrogation session, before the automatic atrial event sensing parameter selection process is started.

Other criteria may be applied by control circuit 206 at block 1001 before starting the selection process. For example, control circuit 206 may verify that the patient activity level is less than a threshold level, verify that a target heart rate for rate responsive pacing based on the patient activity level is less than a threshold rate, and/or verify that the actual ventricular rate is not greater than a threshold rate. In some examples, control circuit 206 may be configured to determine a patient activity metric from the motion sensor signal that is correlated to the level of patient physical activity. This patient activity metric may be used by control circuit to control rate responsive ventricular pacing in some examples, to provide ventricular rate support during times of increased or elevated patient activity.

Upon initiating the atrial event sensing parameter selection process, control circuit 206 may set test values of multiple control parameters to enable motion sensor signal analysis and data collection for generating distribution data for setting atrial event sensing control parameters. At block 1002, control circuit 206 may switch from a programmed atrial tracking ventricular pacing mode, e.g., VDD pacing mode, to a temporary non-atrial tracking ventricular pacing mode, e.g., VDI pacing mode that includes generating the motion sensor signal for analysis. Control circuit 206 may set a temporary lower pacing rate to control the ventricular pacing rate during the motion sensor signal analysis. In one example, the lower pacing rate is set to 50 pulses per minute but may be set to 40 pulses per minute or higher in various examples.

At block 1002, control circuit 206 may set test values for a test A3 threshold amplitude for detecting the latest motion signal threshold crossings during the A3 window for use in establishing the ending time of the A3 window. Additionally or alternatively, control circuit 206 may set one or both of the early and late A4 sensing threshold amplitude values to maximum possible values to avoid actual A4 sensing during the motion sensor signal analysis. In an illustrative example, the A4 sensing threshold amplitude values, both early (during A3 window) and late (during A4 window), may be set to a maximum limit of the ADC or to a value that is beyond the maximum value of the distribution range being generated or the maximum bin range of the histogram being generated of maximum amplitudes of the vector signals being analyzed. In this way, A4 event detections are avoided, which may otherwise terminate the A3 or A4 windows precluding additional analysis of the motion sensor signal during a given ventricular cycle. Control circuit 206 may further set a post ventricular blanking period, and a test setting of the ending time of the A3 window.

As described above, the end of the A3 window (and start of the A4 window) may be set to a percentage of the ventricular rate interval during motion sensor signal analysis. For example, control circuit 206 may determine the ventricular cycle length, which may be paced or sensed, for a specified number of the ventricular cycles upon switching to the VDI pacing mode at block 1002. Control circuit 206 may determine a mean or median value of the determined ventricular cycle lengths and set the test ending time of the A3 window to start at a percentage of the mean or median ventricular cycle length. In one example, the test A3 window ending time is set to 80% of the fourth shortest ventricular cycle length out of the first eight ventricular cycles after switching to the VDI pacing mode. The end of the A3 window (and start of the A4 window) may be set between a specified minimum and maximum time interval, e.g., not less than 650 ms and not more than 900 ms from the most recent ventricular electrical event (sensed or paced) in some examples. When the specified percentage of the median ventricular cycle length falls outside the limited range, the minimum or maximum value may be used instead.

The post-ventricular blanking period may be set to a fixed value, a value based on the lower pacing rate set during the temporary VDI pacing mode, or a median ventricular cycle length. In one example, the post-ventricular blanking period is set to 600 ms when the lower pacing rate is set to 50 pulses per minute. The A3 window starts upon expiration of the post-ventricular blanking period and extends to the test A3 window ending time.

The test A3 threshold amplitude for detecting the latest motion sensor signal threshold crossing during the test A3 window, for use in setting the A3 window ending time, e.g., as described in conjunction with FIGS. 9 and 10, may be set to a relatively low amplitude that is expected to be greater than the baseline motion sensor signal noise. For example, the test A3 threshold amplitude may be set to 9 ADC units, which may correspond to approximately 106 milli-g or about 1 $m/s^2$.

At block 1002, control circuit 206 may establish the vector signals from motion sensor 212 that will be analyzed for generating distribution data. In some examples, each available two-axis vector signal and the three-axis vector signal are generated and analyzed to generate amplitude and timing distribution data for each of the vector signals. For example, referring to each axis of the three-dimensional accelerometer as axis 1, axis 2 and axis 3, a combination of axis 1 and axis 2 may be referred to as the 1+2 vector signal, a combination of axis 1 and axis 3 may be referred to as the 1+3 vector signal, and the combination of axis 2 and axis 3 may be referred to as the 2+3 vector signal. The combination of all three axis signals from the motion sensor 212 may be referred to as the 1+2+3 vector signal. In one example, each of the 1+2 vector signal, 1+3 vector signal, 2+3 vector signal and the 1+2+3 vector signal may be processed and analyzed by control circuit 206 to determine amplitude and timing data of the respective vector signals for selecting at least one atrial event sensing control parameter used during the atrial tracking ventricular pacing mode.

After setting the test pacing mode, pacing rate, test vector signals and other test control parameters, control circuit 206 may begin acquiring amplitude and timing data from the vector signals being analyzed at block 1004. When the four vector signals listed above are selected for analysis during the automatic atrial sensing parameter selection process, each vector signal may be analyzed on a rotating basis to remove or minimize the effects of confounding factors on a particular vector signal, such as posture-dependent changes that may occur in a vector signal due to changing patient position or activity. For example, one vector signal may be analyzed over a one minute time interval for acquiring amplitude and timing data then the next vector signal may be analyzed for the next one minute time interval and so on. In this way, each of the four vector signals listed above may be analyzed over one minute of every four minute time interval. This process may be repeated a specified number of times, e.g., two times, five times, ten times, etc., until a desired number of minutes or data points are obtained for each of the vector signals being analyzed. In one example, amplitude and timing data are obtained from each of the four vector signals listed above on a rotating basis for a total of five minutes per vector signal or for at least 20 minutes total.

In other examples, one or more of the single-axis vector signals, e.g., the axis 1 vector signal, the axis 2 vector signal and/or the axis 3 vector signal may be included as test vector signals in the analysis for obtaining vector signal data at block 1004. Any specified number of vector signals where each vector signal may be obtained from a single accelerometer axis, the sum of two axis signals, or the sum of all three accelerometer axis signals may be included in the analysis for obtaining amplitude and timing data at block 1004. The number of vector signals analyzed and the accelerometer axes used to obtain each vector signal may be programmable by a user. When a combination of axes are used, the signal from each axis of the combination of axes may be sampled at specified time slots of a sampling rate so that the sampled points from two or all three axis signals may be summed to produce the desired vector signal that is a combination of two or all three accelerometer axis signals. For example, if a vector signal is sampled every 1 ms, each axis signal may be sampled for 333 ms time slots so that a sample of each axis signal is available for summing with one or more other axis signals at each 1 ms sample point time.

At block 1004, amplitude and/or timing data is accumulated from the vector signals being analyzed as needed for selecting one or more atrial event sensing parameters. For example, one or more of the A4 sensing vector signal, the early A4 sensing threshold amplitude value, the late A4 sensing threshold amplitude value, and/or the A3 window ending time, or any combination thereof, may be established by control circuit 206 during the process of flow chart 1000. When the process of flow chart 1000 is being performed to select the A4 sensing vector signal, the maximum amplitude during the A4 window is determined from each test vector signal for a desired number of ventricular cycles or time period. By setting the late A4 sensing threshold amplitude value to a relatively high value, e.g., a maximum available value, the A4 window is not terminated before the next ventricular event allowing control circuit 206 to determining the maximum vector signal amplitude until the next ventricular event, paced or sensed.

Other data determined from each of the vector signals may include the time of the latest test A3 threshold crossing during the test A3 window (e.g., as generally described in conjunction with FIGS. 9 and 10) and the maximum vector signal amplitude during the A3 window and/or the A4 window (e.g., as generally described in conjunction with FIGS. 11-13). The amplitude and/or timing data determined from each test vector signal depends on which of the atrial event sensing parameter values that are being set by control circuit 206 during the process of flow chart 1000.

At any time before, during or upon completion of the determination of the amplitude and/or timing data from the motion sensor vector signals at block 1004, control circuit 206 may detect an abort condition as indicated by block 1006. One or more conditions may result in confounding effects on the amplitude and timing data warranting a pause or delay in obtaining the data. For example, high or variable patient physical activity and/or high or variable heart rate may cause changes in the amplitude and timing data for a given vector signal that confounds the distribution data generated for the vector signal. As such, the amplitude and/or timing data acquired at block 1004 for selecting one or more atrial event sensing control parameters may be acquired over time intervals associated with a relatively low, stable heart rate, e.g., less than 80 beats per minute, and/or patient physical activity level, e.g., less than an activity threshold corresponding to activities of daily living or rest.

Control circuit 206 may determine a patient physical activity metric from the motion sensor signal at regular time intervals. A target heart rate and sensor indicated pacing rate may be determined based on the physical activity metric to provide rate responsive pacing to support the level of patient physical activity. Control circuit 206 may detect an abort condition based on at least one patient physical activity metric or level determined from the motion sensor signal as being greater than a threshold activity level. In another example, control circuit 206 may detect an abort condition based the variability of the patient physical activity level, e.g., by detecting a threshold change in the physical activity level within a predetermined time interval. In other examples, control circuit 206 may detect an abort condition in response to determining that the target heart rate, sensor indicated pacing rate and/or actual ventricular rate, paced or sensed, is greater than a threshold rate or is highly variable based on threshold rate change within a predetermined time interval.

In one example, a ventricular rate that is faster than 85 beats per minute may be an abort condition. Control circuit 206 may determine ventricular cycle lengths during the amplitude and timing data acquisition at block 1004. After data acquisition is completed, control circuit 206 may determine if more than a percentage threshold, e.g., more than 20% to 30%, of the ventricular cycle lengths are shorter than a threshold interval at block 1006. For example, if 20% or more of the ventricular cycle lengths during the data acquisition were shorter than about 700 ms (or faster than a rate of about 85 beats per minute), then an abort condition may be detected at block 1006 due to a high ventricular rate. The data may be discarded without generating a distribution or histogram of the data. In other examples, the data may be stored and compiled with data obtained during the next data acquisition time for generating and analyzing a distribution of the data.

The threshold ventricular cycle length interval for detecting a high heart rate may be 650 to 750 ms in other examples. In still other examples, the threshold ventricular cycle length interval may be set based on a mean or median ventricular cycle length determined from the ventricular cycle lengths stored during the data acquisition. For instance, the threshold cycle length may be set to the median ventricular cycle length minus 100 to 150 ms or set to correspond to a ventricular rate that is 10 to 20 beats per minute faster than the median ventricular rate during data acquisition. In an illustrative example, when more than 20% (or other selected percentage) of the ventricular cycle lengths correspond to a ventricular rate that is faster than the rate of the median cycle length during the data acquisition plus 10 beats per minute, an abort condition may be detected at block 1006 due to a variable or high ventricular rate.

An abort condition may be detected at block 1006 due to a variable heart rate that includes a threshold percentage of ventricular cycle lengths longer than a long threshold cycle length (or slower than a corresponding ventricular rate) in some examples. Control circuit 206 may set a long threshold cycle length based on the ventricular rate corresponding to the median ventricular cycle length determined from ventricular cycle lengths stored during the data acquisition of block 1004. For example, the long threshold cycle length may be set to the ventricular rate interval corresponding to the median ventricular rate determined from the median ventricular cycle length during data acquisition minus 10 beats per minute. When more than the threshold percentage (e.g., 20%, 30% or other percentage) of ventricular cycle lengths are longer than a slow ventricular rate interval, e.g., corresponding to 10 beats per minute less than the median rate, an abort condition may be detected due to a variable ventricular rate at block 1006.

Additionally or alternatively, a high or variable patient activity level may be an abort condition detected at block 1006. A patient physical activity metric may be determined by integrating the absolute value of a selected accelerometer vector signal over a predetermined time duration (such as 2 seconds). This metric may be referred to as an "activity count" and is correlated to the acceleration imposed on the motion sensor due to patient body motion associated with physical activity during the predetermined time interval. The 2-second (or other time interval) activity count can be used directly to indicate patient physical activity level in some examples or combined in further calculations to obtain other physical activity metrics. At least one activity count may be compared to a threshold count at block 1006 to determine if an abort condition is met. In some examples, a threshold number of activity counts, e.g., 10 to 40 activity counts, greater than a threshold activity count may be detected as an abort condition. For instance, when 30 activity counts, each determined over 2-second intervals, are greater than a threshold activity count during the data acquisition, control circuit 206 may determine that an abort condition is met at block 1006 due to high patient activity. The activity count threshold may correspond to a patient activity that exceeds activities of daily living, corresponds to brisk walking or other activity level that may be associated with body motion and/or posture changes that may alter the motion sensor signal compared to relatively lower physical activity, e.g., rest or low level activities of daily living.

In other examples, each activity count may be compared to a median activity count, and if more than a threshold percentage of each activity count determined during data acquisition differs from the median activity count by more than a threshold difference (plus or minus), an abort condition may be detected due to variable patient activity at block 1006. In still other examples, a target heart rate or sensor indicated pacing rate may be determined by control circuit 206 based on the activity counts. A target heart rate or sensor indicated pacing rate determined based on a patient physical activity metric may be compared to a threshold rate, e.g., 10 beats per minute greater than the current ventricular rate, and/or rate variability criteria for detecting an abort condition in some examples.

In addition or alternatively to heart rate and/or patient physical activity based abort conditions, control circuit 206 may detect an abort condition in response to telemetry circuit 208 receiving communication signals, e.g., from external device 20. When a telemetry session is initiated and programming commands are being received by telemetry circuit 208, for instance, control circuit 206 may detect an abort condition. In some examples, telemetry circuit 208 may be enabled to transmit the motion sensor signal or related data during the atrial event sensing parameter set-up procedure of flow chart 1000; however other telemetry signals received from external device 20, such as programming commands, may be detected as an abort condition. A programming command includes an instruction to change a programmable control parameter used by control circuit 206 in controlling sensing, therapy delivery or other pacemaker functions.

When an abort condition is detected at block 1006, control circuit 206 may determine if a maximum time period for data acquisition and atrial event sensing parameter selection has been reached at block 1010. If not, control circuit 206 may temporarily abort the data acquisition at block 1012 and return to block 1004 to restart vector signal analysis for acquiring amplitude and timing data. The data acquisition may be restarted on a next processor interrupt signal or after a predetermined time interval, e.g., after one minute, five minutes or other selected time interval. In some examples, control circuit 206 may monitor the ventricular cycle lengths and/or patient physical activity level until the abort condition is no longer detected and restart the data acquisition at block 1004 when a relatively, stable ventricular rate and/or relatively low, stable patient physical activity is detected. In still other examples, when an abort condition is detected, control circuit 206 may wait a predetermined time interval, e.g., one minute, and then resume motion sensor signal data collection. In some cases, data acquired before the abort condition was detected is discarded. In other examples, data acquired before the abort condition was detected is saved and combined with data obtained after resuming data collection.

The data acquisition process may be restarted multiple times up to a maximum number of attempts or over a maximum time period, for example for up to one hour, four hours, 24 hours or other selected maximum attempt time period. If the maximum number of attempts or maximum time period for successfully acquiring the amplitude and timing data for all vector signals being analyzed is expired at block 1010, the process may be terminated at block 1020. The control circuit 206 may terminate any temporary control parameters previously set to test values at block 1002. For example, control circuit 206 may switch back to the programmed pacing mode, e.g., the VDD pacing mode, using any default or programmed atrial sensing control parameters at block 1024. Control circuit 206 may generate a notification at block 1022 indicating the automatic sensing parameter selection process was terminated. The notification generated at block 1022 may include the number of data acquisition attempts or restarts and/or the associated abort condition(s) detected. Any generated notifications may be transmitted by telemetry circuit 208 to external device 20 for display on display unit 54. A user may program atrial sensing control parameters for use during the VDD pacing mode.

When the data acquisition is completed, e.g., five minutes per test vector signal, within the maximum time period, control circuit 206 advances to block 1014 to generate the data distributions, e.g., in the format of histograms as generally shown in FIGS. 8, 10, 12 and 13. Based on the histogram distributions, one or more atrial event sensing parameter values may be selected and set at block 1016. While detection of an abort condition is indicated at block 1106, after acquiring amplitude and/or timing data from the motion sensor vector signals and before generating histogram distributions, it is to be understood that an abort condition may be detected by control circuit 206 before, during, or after acquiring amplitude and timing data (block 1004), generating histogram distributions (block 1014) or selecting the A4 sensing control parameters (block 1016). Monitoring for one or more abort conditions, such as any of the examples described above, may be ongoing during the process of blocks 1001 to 1016 and is not limited to a particular point in time during the process of setting test parameters, acquiring data, generating distributions of the data and selecting A4 sensing control parameters.

In some examples, the A4 sensing vector signal is selected at block 1016 based on the histograms of the maximum vector signal amplitude during the A4 window generated for each vector signal. For each vector signal being analyzed, control circuit 206 may determine a valid maximum amplitude sample count. For example, the maximum amplitudes that are greater than a minimum threshold amplitude, e.g., a minimum programmable value of the late atrial event sensing threshold amplitude may be counted. Any vector signal having a valid maximum amplitude sample count that is less than a rejection threshold number of valid maximum amplitudes may be rejected as a possible A4 sensing vector signal. For instance, when less than 20 of the maximum amplitudes acquired for a given vector signal are determined to be greater than the minimum programmable late atrial event sensing threshold, the vector signal may be rejected from the selection process because the maximum amplitudes acquired for that vector signal meet rejection criteria.

Control circuit 206 may determine the median maximum amplitude out of all maximum amplitudes acquired that are greater than the minimum programmable late atrial event sensing threshold value (or other minimum threshold). The median maximum amplitude may be determined after discarding maximum amplitudes less than a noise threshold for each non-rejected vector signal. For instance, for each vector signal not meeting rejection criteria, the histogram bins that store the number of maximum amplitudes that are less than or equal to a minimum programmable A4 sensing threshold amplitude value may be discarded. A median of the maximum amplitudes may be determined from the distribution of maximum amplitudes in histogram bins greater than the minimum A4 sensing threshold amplitude value. The vector signal corresponding to the highest median maximum amplitude determined from the A4 windows may be selected as the A4 sensing vector signal at block 1016.

In the illustrative example given above of analyzing each of the four vector signals designated by the accelerometer axis combinations of 1+2, 1+3, 2+3 and 1+2+3, if all three of the two-axis signals have fewer than the threshold number of valid maximum amplitude sample points, the three-axis vector signal may be selected as the A4 sensing vector signal at block 1016. When at least one of the three two-axis vector signals has the requisite number of valid maximum amplitude sample points, the two-axis vector signal having the highest median maximum amplitude may be selected as the A4 sensing vector signal (e.g., to conserve current drain required to power the third accelerometer axis). When two or more of the two-axis vector signals have the same median maximum amplitude during the A4 window, a two-axis vector signal sharing the single axis used for determining patient physical activity may be selected. In other examples, the single-axis vector having the highest median maximum amplitude may be identified and any two-axis vector signal including the single-axis vector signal having the highest median maximum amplitude may be selected. In one example, when axis 2 is generally aligned with the longitudinal axis 108 of pacemaker 14 (see FIG. 2), priority is given to the 1+2 vector signal, then the 2+3 vector signal then the 1+3 vector signal when the median maximum amplitude of the A4 window matches between two or all three of the vector signals. The single-axis vector signal generally aligned with the longitudinal axis of the pacemaker 14 may correspond to the highest A4 signal amplitude though this may vary with implant position and orientation. The single axis vector signal having the highest A4 signal amplitude may be identified from empirical data, and any two-axis vector signal including this identified single-axis vector may be given priority when two or more two-axis vector signals have equal median maximum amplitudes.

At block 1016, control circuit 206 may set the late A4 sensing threshold amplitude value (applied during the A4 window during atrial tracking ventricular pacing) based on the median value of the maximum amplitudes determined during the A4 window for the selected A4 sensing vector signal. In one example, the late A4 sensing threshold amplitude value is set to the median value of the maximum amplitudes determined during the A4 window for the selected A4 sensing vector signal. In other examples, the late A4 sensing threshold amplitude value is set to a percentage, e.g., 60 to 80% of the median maximum amplitude value. In some cases, the method of setting the late A4 sensing threshold amplitude value depends on the median maximum amplitude during the A4 window. For example, if the median maximum amplitude during the A4 window is 1.2 m/s$^2$ (or other threshold acceleration), the late A4 sensing threshold amplitude may be set to the median maximum amplitude. If the median maximum amplitude is greater than 1.2 m/s$^2$ (or other threshold acceleration), the late A4 sensing threshold amplitude may be set to 70% of the median maximum amplitude of the A4 window, but not less than 1.2 m/s$^2$ (or other minimum limit).

The method for setting the late A4 sensing threshold amplitude value may differ depending on the selected A4 sensing vector signal. For example, the late A4 sensing threshold amplitude may be set according to a percentage of the median or at least a minimum limit when a two-axis vector signal is selected as the A4 sensing vector signal. The late A4 sensing threshold amplitude may be set according to a different percentage or limit when the three-axis vector signal is selected as the A4 sensing vector signal. The late A4 sensing threshold amplitude may be set within lower and upper limits, e.g., between 0.5 m/s$^2$ and 5.0 m/s$^2$. The minimum A4 sensing threshold amplitude may be different depending on the number of accelerometer axis signals being combined in the selected vector signal. For example, a relatively low minimum threshold amplitude, e.g., 0.6 m/s$^2$, may be enforced for a single-axis vector signal; an intermediate minimum threshold amplitude, e.g., 0.7 m/s$^2$, may be enforced for a two-axis vector signal, and the highest minimum threshold amplitude, e.g., 0.8 m/s$^2$, may be enforced for a three-axis vector signal. A relatively higher minimum threshold amplitude setting may be allowable for vector signals that are a combination of two or all three accelerometer axis signals compared to single-axis vector signals because with the addition of each axis signal additional noise is included in the summed axis signals.

Control circuit 206 may set an early A4 sensing threshold amplitude (applied during the A3 window during atrial tracking ventricular pacing) at block 1016. The early A4 sensing threshold amplitude may be set based on the maximum amplitudes determined during the A3 window for the selected A4 sensing vector signal. In one example, the early A4 sensing threshold amplitude value is set by determining the median maximum amplitude during the A3 window (for the selected A4 sensing vector signal), multiplying this median maximum amplitude by a multiplication factor, e.g., 1.5, and adding this product of the median maximum amplitude and the multiplication factor to the late A4 sensing threshold amplitude. In some example, setting the early A4 sensing threshold amplitude value may include adding an offset, e.g., by adding 0.3 m/s$^2$. The early A4 sensing threshold amplitude may be set based on the median maximum amplitude during the A4 window, the median maximum amplitude during the A3 window, or a combination of both which may be a weighted combination. The early A4 sensing threshold amplitude may be set within upper and lower limits, e.g., between 0.8 m/s$^2$ and 18.8 m/s$^2$ in one instance.

Control circuit 206 may set an A3 window ending time at block 1016 based on the distribution of the timing of the latest test threshold crossing during the A3 window determined for the selected A4 sensing vector signal. In one example, the A3 window ending time is set based on the median time of the latest test threshold crossing during the A3 window plus an offset, e.g., plus 50 to 150 ms. The A3 window ending time may be set within minimum and maximum limits, e.g., not less than 650 ms and not more than 1000 ms.

Upon completing the atrial event sensing control parameter selection at block 1016, control circuit 206 may generate a notification at block 1022 that parameter selection was complete, including selected parameters. The selected parameters may be transmitted by telemetry circuit 208 to external device 20 for generating a display of the results of the automatic set-up procedure. Control circuit 206 may switch to the atrial tracking ventricular pacing mode, e.g., the VDD pacing mode, at block 1024 with the selected A4 sensing control parameters in effect.

In some instances, the maximum amplitude during the A4 window may be too low to reliably select A4 sensing control parameters. For example, when fewer than a threshold number of sample points exceed the minimum programmable late A4 sensing threshold amplitude value for all vector signals, control circuit 206 may set the A4 sensing control parameters to default or previous settings and generate a notification indicating a low A4 signal amplitude at block 1022. The notification may be transmitted by pacemaker 14 and displayed by external device 20, allowing a user to select and program the pacing mode and sensing control parameters.

Figure 16:
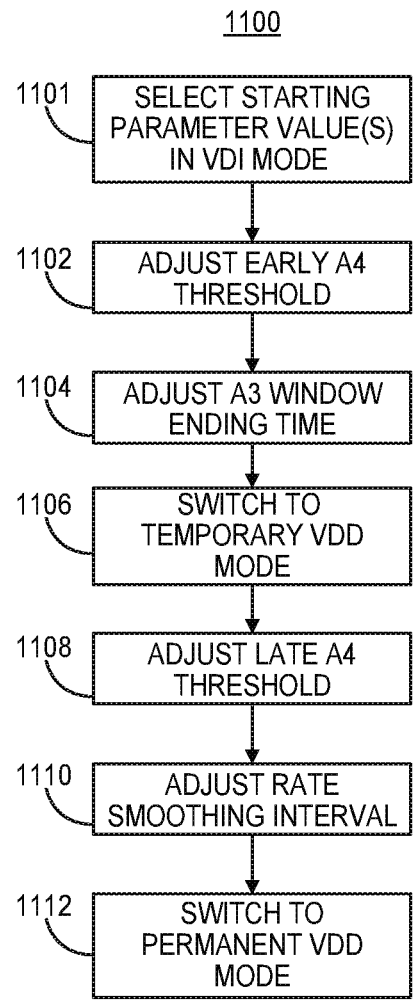
FIG. 16 is a flow chart of a method for setting and adjusting atrial event sensing control parameters according to one example.

FIG. 16 is a flow chart 1100 of a method for adjusting selected atrial event sensing control parameters according to one example. Control circuit 206 may determine a starting value of one or more A4 sensing control parameters at block 1101, such as the A3 window ending time and the early and late A4 sensing threshold amplitude values using the techniques described above in conjunction with FIGS. 6-15. After selecting a starting value, the starting value may be adjusted to an operational value used upon switching to the permanent atrial tracking ventricular pacing mode. At block 1102 and block 1104, control circuit 206 may continue to operate in the non-atrial tracking ventricular pacing mode, e.g., in the VDI pacing mode, to enable adjusting of the early A4 sensing threshold amplitude value from its selected starting value and adjusting of the A3 window ending time from its selected starting value.

At block 1102, control circuit 206 may continue operating in the VDI pacing mode, and update the early A4 threshold amplitude value based on the maximum amplitude of the selected vector signal during the A3 window determined from one or more ventricular cycles. In one example, the median maximum amplitude during the A3 window may be determined from a predetermined number of consecutive ventricular cycles, e.g., 3 to 12 ventricular cycle. For instance, the early A4 threshold amplitude value may be adjusted after every eight ventricular cycles based on a median maximum amplitude of the selected vector signal determined during the eight ventricular cycles. The median maximum amplitude of the A3 window may be determined from 8 consecutive ventricular cycles as the 4$^{th}$ highest maximum amplitude in one example. In some examples, a target value of the early A4 threshold amplitude value may be determined based on the median maximum amplitude determined. The starting value of the early A4 threshold amplitude determined during the set up process may be adjusted by a predetermined increment or decrement toward the target value. The predetermined increment or decrement may be 0.1 to 0.5 m/s$^2$ and is 0.3 m/s$^2$ in one example. This process may repeat every 8 ventricular cycles (or other predetermined number of cycles) for an adjustment time interval, e.g., for one minute, two minutes, five minutes or other selected time interval, while operating in the VDI pacing mode. The adjusted starting early A4 threshold amplitude value may not go into effect until control circuit 206 switches to an atrial tracking ventricular pacing mode such that A4 events are not being detected until all atrial event sensing parameters are adjusted to an operational value from the starting value determined based on the distributions of data described above.

At block 1104, control circuit 206 may determine the time of the latest test threshold amplitude crossing of the selected vector signal during the A3 window for one or more consecutive ventricular cycles. The starting A3 window ending time may be adjusted based on the latest test threshold crossing time during the A3 window determined from the one or more ventricular cycles. The test threshold amplitude may be set to a percentage, e.g., 75%, of the late A4 sensing threshold amplitude value set during the set up procedures described above. The A3 window ending time established during the set up procedure is based on the latest crossing of a test threshold that may set to a predetermined, fixed value, e.g., 0.9 m/s$^2$. However, the starting late A4 threshold amplitude determined during the set up process for the selected vector is tailored to the patient and selected atrial event sensing vector and A4 signal amplitude. A test threshold set to a percentage of the starting late A4 threshold amplitude may be a more appropriate threshold for determining latest threshold crossing times and setting the A3 window ending time. For example, if the starting value of late A4 threshold amplitude is set to 2.5 m/s$^2$ at the end of the set up process at block 1101, a test threshold set to 75% of the late A4 threshold amplitude is 1.9 m/s$^2$. This test threshold may be used during the A3 window for detecting the latest test threshold crossing times for adjusting the A3 window ending time to provide optimization of the A3 window ending time tailored to the patient for the selected sensing vector.

The median of the latest test threshold crossing times during the A3 window may be updated after every 3 to 12 ventricular cycles. The median time of the latest A3 threshold amplitude crossing may be determined as the 4$^{th}$ shortest time out of 8 ventricular cycles. The median of the latest test threshold crossing times may be used to update the A3 window ending time established during the set up procedures described above. A target A3 window ending time may be set based on the median time. The A3 window ending time may be adjusted from the current value of the A3 window ending time plus or minus an adjustment interval toward the target value. The A3 window ending time may be adjusted every 8$^{th}$ ventricular cycle, or other selected number of ventricular cycles, for 2 minutes (or other adjustment time interval) to arrive at an adjusted starting A3 window ending time that goes into effect as the operational A3 window ending time upon switching to an atrial tracking ventricular pacing mode (e.g., VDD pacing mode).

After adjusting the A3 window ending time and/or the early A4 sensing threshold value from their respective set up starting values to operational values during the VDI pacing mode, control circuit 206 may switch to a temporary atrial tracking pacing mode (e.g., VDD pacing mode) at block 1106. The operational values of the early A4 sensing threshold amplitude value and the A3 window ending value may be in effect upon switching to the temporary VDD pacing mode.

The late A4 sensing threshold amplitude value may be adjusted from its starting value at block 1108. During this temporary VDD pacing mode, the late A4 sensing threshold amplitude value may be adjusted from its starting value based on the maximum amplitude of the selected sensing vector signal during one or more A4 windows. In one example, control circuit 206 determines a median maximum amplitude during the A4 window of the selected vector signal after every X ventricular cycles. An adjusted late A4 sensing threshold amplitude value may be determined based on the determined median. In some examples, a target late A4 sensing threshold amplitude value may be determined based on the median determined every eight ventricular cycles. The starting value of the late A4 sensing threshold amplitude may be adjusted up or down by a predetermined adjustment interval, e.g., ±0.3 m/s$^2$, toward the updated target late A4 sensing threshold. This process may be repeated every X ventricular cycles for a predetermined time interval, e.g., every eight ventricular cycles for two minutes, during the VDD pacing mode to arrive at an operational late A4 sensing threshold amplitude value.

At block 1110, control circuit 206 may determine a rate smoothing interval based on one or more ventricular cycle lengths during the temporary VDD pacing mode. In some examples, the starting rate smoothing interval is set to the programmed lower rate interval. The median ventricular cycle length over X ventricular cycles, e.g., eight ventricular cycles may be determined. An adjusted rate smoothing interval may be set to a predetermined interval longer than the median ventricular cycle length, e.g., 100 to 150 ms longer than the median ventricular cycle length. The rate smoothing interval may be updated every X ventricular cycles for a predetermined time interval, e.g., two minutes.

After adjusting the starting value of the late A4 sensing threshold amplitude and adjusting the rate smoothing interval during the temporary VDD pacing mode, control circuit 206 may switch to a permanent atrial tracking pacing mode at block 1112 with the operational values of the A4 sensing control parameters and adjusted rate smoothing interval in effect. In this way, starting values of the A4 sensing control parameters determined during the automatic set up processes described above, and the rate smoothing interval, can be adjusted to operational values that are set and take effect according to the contemporaneous signal amplitude and timing features of the selected vector signal and current ventricular rate.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A pacemaker comprising:
   a pulse generator configured to generate pacing pulses;
   a sensing circuit comprising an R-wave detector for sensing R-waves from a cardiac electrical signal;
   a motion sensor configured to produce a motion signal comprising an atrial event signal corresponding to an atrial systolic event; and
   a control circuit coupled to the motion sensor and the pulse generator and configured to:
      identify a plurality of ventricular electrical events, wherein each of the plurality of ventricular electrical events is one of an R-wave sensed by the sensing circuit or a ventricular pacing pulse generated by the pulse generator;
      following each of at least a portion of the plurality of ventricular electrical events, set a sensing window;
      determine a feature of the motion signal during each of the sensing windows by determining a latest crossing time of a first threshold amplitude by the motion signal during each of the sensing windows;
      set an atrial event sensing parameter by setting an ending time of a passive ventricular filling window based on the determined features;
      sense the atrial systolic event based on the atrial event sensing parameter; and
      produce an atrial sensed event signal in response to sensing the atrial systolic event.

2. The pacemaker of claim 1, wherein the control circuit is configured to:
   set the passive ventricular filling window following each of at least a portion of the plurality of ventricular electrical events;
   set an atrial event sensing window starting at the ending time of the passive ventricular filling window;
   during each atrial event sensing window, determine a first maximum amplitude of the motion signal;
   determine a distribution of the first maximum amplitudes; and
   set a late atrial event sensing threshold amplitude based on the distribution.

3. The pacemaker of claim 2, wherein the control circuit is configured to:
   determine second maximum amplitudes of the motion signal during each passive ventricular filling window; and
   set an early atrial event sensing threshold based on the maximum amplitudes of the motion signal during the passive ventricular filling window.

4. The pacemaker of claim 3, wherein the control circuit is configured to set the early atrial event sensing threshold by determining a weighted sum of a median of the first maximum amplitudes and a median of the second maximum amplitudes.

5. The pacemaker of claim 2, wherein the control circuit is configured to:
   discard first maximum amplitudes that are less than a noise threshold;
   determine one of a percentile and a median of the first maximum amplitudes after discarding the first maximum amplitudes that are less than the noise threshold; and
   set the late atrial event sensing threshold amplitude based on the determined one of the percentile and the median.

6. The pacemaker of claim 1, wherein the control circuit is further configured to:
   set the passive ventricular filling window following each of at least a portion of the plurality of ventricular electrical events;
   determine a maximum amplitude of the motion signal during each of the passive ventricular filling windows;
   determine a distribution of the maximum amplitudes;
   set an early atrial event sensing threshold amplitude based on the distribution of the maximum amplitudes.

7. The pacemaker of claim 6, wherein the control circuit is configured to sense the atrial systolic event in response to an earliest one of:
   the motion signal crossing the early atrial event sensing threshold amplitude during the passive ventricular filling window; and
   the motion signal crossing a late atrial event sensing threshold amplitude after the passive filling window, the late atrial event sensing threshold amplitude being less than the early atrial event sensing threshold amplitude.

8. The pacemaker of claim 1, wherein the control circuit is further configured to:
   detect an abort condition after starting to determine the feature of the motion signal; and
   abort determining the feature of the motion signal in response to detecting the abort condition.

9. The pacemaker of claim 8, wherein the control circuit is configured to detect the abort condition by detecting one of:
   a change in heart rate;
   a change in patient physical activity; and
   a telemetry communication signal received from another medical device.

10. The pacemaker of claim 1, wherein the control circuit is further configured to:
    determine a median of the determined features; and
    set the atrial event sensing parameter based on the median.

11. The pacemaker of claim 1, wherein the control circuit is further configured to:
    determine a distribution of the determined features; and
    set the atrial event sensing parameter based on a percentile of the distribution.

12. The pacemaker of claim 1, wherein the control circuit is further configured to:
    set a non-atrial tracking pacing mode prior to identifying the plurality of ventricular electrical events;
    determine the feature of the motion signal during each of the sensing windows during the non-atrial tracking pacing mode;

switch to an atrial tracking pacing mode after setting the atrial event sensing parameter; and
sense the atrial systolic event from the motion signal using the set atrial event sensing parameter during the atrial tracking pacing mode.

13. The pacemaker of claim 1, wherein:
the motion sensor is a multi-axis motion sensor configured to produce an axis signal from each axis;
the control circuit is further configured to:
  determine a maximum amplitude of each one of a plurality of vector signals after each of the sensing windows, each one of the plurality of vector signals comprising one or more of the axis signals;
  determine a distribution of the maximum amplitude after the sensing window for each one of the plurality of vector signals;
  determine one of the plurality of vector signals having a greatest median of the distribution of the maximum amplitudes after the sensing window; and
  select an atrial event sensing vector signal as the one of the plurality of vector signals having the greatest median of the distribution of the maximum amplitudes after the sensing windows.

14. The pacemaker of claim 1, wherein the control circuit is configured to:
discard latest crossing times that are greater than an atrial event confidence time threshold; and
set the ending time of the passive ventricular filling window based on a distribution of the latest crossing times that are less than the atrial event confidence time threshold.

15. The pacemaker of claim 1, wherein the control circuit is further configured to:
determine a median from the latest crossing times; and
set the ending time of the passive ventricular filling window to the median plus an offset.

16. The pacemaker of claim 1, wherein the control circuit is further configured to:
set a second sensing threshold amplitude; and
sense the atrial systolic event in response to the motion signal crossing the second sensing threshold amplitude later than the ending time of the passive ventricular filling window.

17. The pacemaker of claim 1, wherein:
the control circuit is further configured to start an atrioventricular pacing interval in response to the atrial sensed event signal; and
the pulse generator is configured to generate a ventricular pacing pulse in response to the atrioventricular pacing interval expiring.

18. The pacemaker of claim 1, further comprising a telemetry circuit configured for receiving a communication signal from another medical device;
the control circuit being further configured to:
  wait a time delay after the telemetry circuit stops receiving the communication signal;
  start determining the feature of the motion signal during each of the sensing windows after the time delay.

19. The pacemaker of claim 1, wherein the control circuit is further configured to:
determine the feature of the motion signal during a predetermined number of ventricular cycles after setting the atrial event sensing parameter;
adjust the atrial event sensing parameter based on the feature determined during the predetermined number of ventricular cycles; and
sense the atrial systolic event from the motion signal after adjusting the atrial event sensing parameter.

20. A method, comprising:
producing a motion signal comprising an atrial event signal corresponding to an atrial systolic event;
identifying a plurality of ventricular electrical events, wherein each of the plurality of ventricular electrical events is one of an intrinsic R-wave or a generated ventricular pacing pulse;
following each of at least a portion of the plurality of ventricular electrical events, setting a sensing window;
determining a feature of the motion signal during each of the sensing windows by determining a latest crossing time of a first threshold amplitude by the motion signal during each of the sensing windows;
setting an atrial event sensing parameter by setting an ending time of a passive ventricular filling window based on the determined features;
sensing the atrial systolic event based on the atrial event sensing parameter; and
producing an atrial sensed event signal in response to sensing the atrial systolic event.

21. The method of claim 20, further comprising:
setting the passive ventricular filling window following each of at least a portion of the plurality of ventricular electrical events;
setting an atrial event sensing window starting at the ending time of the passive ventricular filling window;
during each atrial event sensing window, determining a first maximum amplitude of the motion signal;
determining a distribution of the first maximum amplitudes; and
setting a late atrial event sensing threshold amplitude based on the distribution.

22. The method of claim 21, further comprising:
determining second maximum amplitudes of the motion signal during each passive ventricular filling window; and
setting an early atrial event sensing threshold based on the second maximum amplitudes of the motion signal during the passive ventricular filling window.

23. The method of claim 22, wherein setting the early atrial event sensing threshold comprises:
determining a weighted sum of a median of the first maximum amplitudes and a median of the second maximum amplitudes.

24. The method of claim 21, further comprising:
discarding first maximum amplitudes that are less than a noise threshold;
determining one of a percentile and a median of the first maximum amplitudes after discarding the first maximum amplitudes that are less than the noise threshold; and
setting the late atrial event sensing threshold amplitude based on the determined one of the percentile and the median.

25. The method of claim 20, further comprising:
setting the passive ventricular filling window following each of at least a portion of the plurality of ventricular electrical events;
determining a maximum amplitude of the motion signal during each of the passive ventricular filling windows;
determining a distribution of the maximum amplitudes;
setting an early atrial event sensing threshold amplitude based on the distribution of the maximum amplitudes.

26. The method of claim 25, further comprising sensing the atrial systolic event in response to an earliest one of:

the motion signal crossing the early atrial event sensing threshold amplitude during the passive ventricular filling window; and the motion signal crossing a late atrial event sensing threshold amplitude after the passive filling window, the late atrial event sensing threshold amplitude being less than the early atrial event sensing threshold amplitude.

27. The method of claim 20, further comprising:
detecting an abort condition after starting to determine the feature of the motion signal; and
aborting determining the feature of the motion signal in response to detecting the abort condition.

28. The method of claim 27, wherein detecting the abort condition by detecting one of:
a change in heart rate;
a change in patient physical activity; and
a telemetry communication signal received from another medical device.

29. The method of claim 20, further comprising:
determining a median of the determined features; and
setting the atrial event sensing parameter based on the median.

30. The method of claim 20, further comprising:
determining a distribution of the determined features; and
setting the atrial event sensing parameter based on a percentile of the distribution.

31. The method of claim 20, further comprising:
setting a non-atrial tracking pacing mode prior to identifying the plurality of ventricular electrical events;
determining the feature of the motion signal during each of the sensing windows during the non-atrial tracking pacing mode;
switching to an atrial tracking pacing mode after setting the atrial event sensing parameter; and
sensing the atrial systolic event from the motion signal based on the set atrial event sensing parameter during the atrial tracking pacing mode.

32. The method of claim 20, further comprising:
determining a maximum amplitude of each one of a plurality of vector signals after each of the sensing windows, where each one of the plurality of vector signals comprises at least one axis signal produced by a multi-axis motion sensor that is producing the motion signal;
determining a distribution of the maximum amplitude after the sensing window for each one of the plurality of vector signals;
determine one of the plurality of vector signals having a greatest median of the distribution of the maximum amplitudes after the sensing window; and
select an atrial event sensing vector as a vector signal as the one of the plurality of vector signals having the greatest median of the distribution of the maximum amplitudes after the sensing window.

33. The method of claim 20, further comprising:
discarding latest crossing times of the distribution that are greater than an atrial event confidence time threshold; and setting the ending time of the passive ventricular filling window based on a distribution of the latest crossing times that are less than the atrial event confidence time threshold.

34. The method of claim 20, further comprising:
determining a median from the latest crossing times; and
setting the ending time of the passive ventricular filling window to the median plus an offset.

35. The method of claim 20, further comprising:
setting a second threshold amplitude; and
sensing the atrial systolic event in response to the motion signal crossing the second sensing threshold amplitude later than the ending time of the passive ventricular filling window.

36. The method of claim 20, further comprising
starting an atrioventricular pacing interval in response to the atrial sensed event signal; and
generating a ventricular pacing pulse in response to the atrioventricular pacing interval expiring.

37. The method of claim 20, further comprising:
receiving a communication signal from another medical device;
waiting a time delay after receiving the communication signal has stopped;
starting determining the feature of the motion signal during each of the sensing windows after the time delay.

38. The method of claim 20, further comprising:
determining the feature of the motion signal during a predetermined number of ventricular cycles after setting the atrial event sensing parameter;
adjusting the atrial event sensing parameter based on the feature determined during the predetermined number of ventricular cycles; and
sensing the atrial systolic event from the motion signal after adjusting the atrial event sensing parameter.

39. A non-transitory, computer-readable storage medium comprising a set of instructions which, when executed by a control circuit of a pacemaker, cause the pacemaker to:
produce a motion signal comprising an atrial event signal corresponding to an atrial systolic event;
identify a plurality of ventricular electrical events, wherein each of the plurality of ventricular electrical events is one of an intrinsic R-wave or a generated ventricular pacing pulse;
following each of the plurality of ventricular electrical events, set a sensing window;
determining a feature of the motion signal during each of the sensing windows by determining a latest crossing time of a threshold amplitude by the motion signal during each of the sensing windows;
setting an atrial event sensing parameter by setting an ending time of a passive ventricular filling window based on the determined features;
sensing the atrial systolic event based on the atrial event sensing parameter; and
producing an atrial sensed event signal in response to sensing the atrial systolic event.

* * * * *